(12) United States Patent
Berner et al.

(10) Patent No.: US 9,000,046 B2
(45) Date of Patent: Apr. 7, 2015

(54) GASTRIC RETENTIVE DOSAGE FORMS FOR EXTENDED RELEASE OF ACAMPROSATE INTO THE UPPER GASTROINTESTINAL TRACT

(75) Inventors: Bret Berner, Half Moon Bay, CA (US); Cuiping Chen, Palo Alto, CA (US)

(73) Assignee: Depomed, Inc., Newark, CA (US)

( * ) Notice: Subject to any disclaimer, the term of this patent is extended or adjusted under 35 U.S.C. 154(b) by 465 days.

(21) Appl. No.: 13/247,956

(22) Filed: Sep. 28, 2011

(65) Prior Publication Data

US 2012/0077878 A1 Mar. 29, 2012

Related U.S. Application Data

(60) Provisional application No. 61/387,368, filed on Sep. 28, 2010.

(51) Int. Cl.

| A61K 31/16 | (2006.01) |
| A61K 9/22 | (2006.01) |
| A61K 9/26 | (2006.01) |
| A61K 31/185 | (2006.01) |
| A61K 9/00 | (2006.01) |
| A61K 9/20 | (2006.01) |

(52) U.S. Cl.
CPC .............. *A61K 31/185* (2013.01); *A61K 9/0065* (2013.01); *A61K 9/2027* (2013.01); *A61K 9/2031* (2013.01); *A61K 9/2054* (2013.01)

(58) Field of Classification Search
CPC . A61K 31/185; A61K 9/0065; A61K 9/2027; A61K 9/2031
See application file for complete search history.

(56) References Cited

U.S. PATENT DOCUMENTS

| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,014,334 | A | 3/1977 | Theeuwes et al. |
| 4,058,122 | A | 11/1977 | Theeuwes et al. |
| 4,116,241 | A | 9/1978 | Theeuwes et al. |
| 4,160,452 | A | 7/1979 | Theeuwes |
| 4,892,778 | A | 1/1990 | Theeuwes et al. |
| 4,940,465 | A | 7/1990 | Theeuwes et al. |
| 4,996,058 | A | 2/1991 | Sinnreich |
| 5,747,475 | A | 5/1998 | Nordquist et al. |
| 5,866,585 | A | 2/1999 | Fogel |
| 5,952,389 | A | 9/1999 | Fogel |
| 6,057,373 | A | 5/2000 | Fogel |
| 6,117,877 | A | 9/2000 | Fogel |
| 6,159,944 | A | 12/2000 | Fogel |
| 6,245,357 | B1 | 6/2001 | Edgren et al. |
| 6,294,583 | B1 | 9/2001 | Fogel |
| 6,340,475 | B2 | 1/2002 | Shell et al. |
| 6,368,626 | B1 | 4/2002 | Bhatt et al. |
| 6,391,922 | B1 | 5/2002 | Fogel |
| 6,426,087 | B1 * | 7/2002 | Saslawski et al. ............. 424/450 |
| 6,488,962 | B1 | 12/2002 | Berner et al. |
| 6,635,280 | B2 | 10/2003 | Shell et al. |
| 6,689,816 | B2 | 2/2004 | Fogel |
| 6,723,340 | B2 | 4/2004 | Gusler et al. |
| 7,405,238 | B2 | 7/2008 | Markey et al. |
| 7,498,361 | B2 | 3/2009 | Fogel |
| 7,745,493 | B2 | 6/2010 | Fogel |
| 2003/0104062 | A1 | 6/2003 | Berner et al. |
| 2004/0192683 | A1 | 9/2004 | Moormann et al. |
| 2008/0206350 | A1 | 8/2008 | Gryczke |
| 2009/0028941 | A1 | 1/2009 | Cowles et al. |

FOREIGN PATENT DOCUMENTS

WO     WO 03/035177 A2     5/2003

OTHER PUBLICATIONS

Chabenat et al., "Physicochemical, pharmacological and pharmacokinetic study of a new GABAergic compound, calcium acetylhomotaurinate", Meth. Find. Exp. Clin. Pharmacol., vol. 10, No. 5, pp. 311-317 (1988).
Dave et al., "Gastroretentive drug delivery system of ranitidine hydrochloride: formulation and in vitro evaluation", AAPS PharmSciTech, vol. 5, No. 2, 6 pgs. (2004).
Hou et al., "Gastric retentive dosage forms: a review", Crit. Rev. Ther. Drug Carrier Syst., vol. 20, No. 6, pp. 461-497 (2003).
Mas-Serrano et al., "Kinetic study of acamprosate absorption in rat small intestine", Alcohol Alcohol., vol. 35, pp. 324-330 (2000).
Narendra et al., "Optimization of bilayer floating tablet containing metoprolol tartrate as a model drug for gastric retention", AAPS PharmSciTech, vol. 7, No. 2, 7 pgs. (2006).
Zornoza et al., "Pharmacology of acamprosate: an overview", CNS Drug Reviews, vol. 9, pp. 359-374 (2003).
International Search Report from PCT Patent Application No. PCT/US2011/053769 mailed Apr. 10, 2012, 5 pgs., application now published as WO2012/050922 on Apr. 19, 2012.

* cited by examiner

*Primary Examiner* — Sreeni Padmanabhan
*Assistant Examiner* — Jody Karol
(74) *Attorney, Agent, or Firm* — McDermott Will & Emery LLP

(57) ABSTRACT

Gastric retentive dosage forms for sustained release of acamprosate are described which may allow once- or twice-daily dosing for both acute and long-term treatment of a disorder including alcohol dependence, tinnitus, sleep apnea, Parkinson's disease, levodopa-induced dyskinesias in Parkinson's disease, Alzheimer's disease, Huntington's disease, Amyotrophic lateral sclerosis, Cortical spreading depression, migraine, schizophrenia, anxiety, tardive dyskinesia, spasticity, multiple sclerosis, various types pain, or binge eating. Methods of treatment using the dosage forms and methods of making the dosage forms are also described.

11 Claims, 3 Drawing Sheets

GASTRIC RETENTIVE DOSAGE FORMS FOR EXTENDED RELEASE OF ACAMPROSATE INTO THE UPPER GASTROINTESTINAL TRACT

This application claims the benefit of U.S. Provisional Application No. 61/387,368, filed Sep. 28, 2010, the contents of which are incorporated herein by reference in their entirety.

TECHNICAL FIELD

The present subject matter relates generally to dosage forms for extended release of acamprosate into the stomach of a patient in the fed mode and to methods of treatment using the dosage forms.

BACKGROUND

Acamprosate (calcium bis acetyl-homotaurine), is a synthetic analog of γ-amino butyric acid (GABA) and is used as an adjunct for treatment of alcohol dependence. Alcohol dependence is a chronic relapsing medical disorder which bears many of the characteristics of other medical relapsing disorders such as diabetes and hypertension. Without pharmacological treatment to accompany psychotherapy, up to 70% of patients resume drinking within one year (see Bankole et al., Biochem Pharmacol., 2008, 75:34-56).

As alcohol inhibits the activity of N-methyl-D-aspartate receptors (NMDARs), chronic alcohol consumption leads to the upregulation of these receptors. Sudden alcohol abstinence results in excessive activation of NMDARs, leading to symptoms such as delirium tremens and excitotoxic neuronal death (Tsai et al., Ann Rev Med, 1998, 155:726-732; Tsai et al., Am J Psych, 1998, 155:726-732). Acamprosate reduces this effect in vivo. Studies have also suggested that acamprosate protects cultured cells in excitotoxicity induced by ethanol withdrawal, and by glutamate exposure combined with ethanol withdrawal.

Absorption of acamprosate following oral administration occurs via both passive diffusion through the intestinal epithelium and active uptake via amino acid transporter that are expressed in the small intestine (Mas-Serrano et al., Alcohol & Alcoholism, 2000, 35:324-330). Acamprosate exhibits poor absorption in the intestine after oral dosing. It is thought this is primarily due to poor permeability in the intestinal epithelium. Moreover, the uptake transporter in the small intestine becomes saturated with the current dosage form at the dose of 2×333 mg, equivalent to 600 mg of acamprosate free acid, three times daily. Poor absorption not only reduces therapeutic effectiveness of an acamprosate oral dosage form, but also unabsorbed drug passes to the lower GI, resulting in adverse side effects such as diarrhea. Some of these and other side effects are related to the large amounts of calcium, and replacement or elimination of calcium with other cations, e.g., magnesium or sodium, may be beneficial.

Accordingly, it would be useful to manufacture an oral dosage form which is able to provide prolonged and steady levels of acamprosate to the small intestine at concentrations which allow optimal uptake by the intestinal transporter and an effectively longer time for intestinal absorption.

Gastric retained forms that can form the basis for the sustained release of a drug have been previously described, for example, in Gusler et al. (U.S. Pat. No. 6,723,340), Berner et al. (U.S. Pat. No. 6,488,962), Shell et al., (U.S. Pat. No. 6,340,475) and Shell et al. (U.S. Pat. No. 6,635,280). These formulations make use of one or more hydrophilic polymers which swell upon intake of water from gastric fluid. Thus, when administered in the fed mode, when the diameter of the pyloric sphincter is contracted and reduced, the dosage form will swell to a size to be retained in the stomach for a minimum of four hours or more. These formulations may be designed to produce desired release and delivery profiles for both highly soluble and poorly soluble drugs.

As presently disclosed, gastric retentive dosage forms are formulated specifically to provide extended release of acamprosate or of a salt or prodrug of acetyl homotaurine from the stomach into the upper gastrointestinal tract, resulting in prolonged exposure and lower but steady release rate of the acamprosate or related salt or prodrug to the small intestine to optimize uptake and enhance bioavailability. These gastric retentive dosage forms are proposed to be administered with a meal. Gastric retentive dosage forms are generally applicable to drugs where the bioavailability improves when administered with a meal. Since the AUC and Cmax of the current acamprosate dosage form decrease by 23% and 42%, respectively, when administered with food instead of fasting, it is surprising that acamprosate can be administered with good bioavailability from a gastric retentive dosage form that depends on administration in the fed mode.

BRIEF SUMMARY

The present disclosure provides, among other aspects, gastric retentive dosage forms for oral administration to a subject, such as a human patient, for the treatment of alcohol dependence, tinnitus, sleep apnea, levodopa-induced dyskinesias in Parkinson's disease, Alzheimer's disease, Huntington's disease, amyotrophic lateral sclerosis, cortical spreading depression, migraine, schizophrenia, anxiety disorders, motion disorders, tardive dyskinesia, spasticity, multiple sclerosis, various types pain, or binge eating. The dosage form in some embodiments is a gastric retentive dosage form that contains a dose of acamprosate in an extended release ("ER") formulation.

In a first aspect, a gastric retained extended release (ER) oral dosage form comprising a dose of acamprosate dispersed in a polymer matrix comprising at least one hydrophilic polymer is provided. Upon administration, the polymer matrix swells upon imbibition of fluid to a size sufficient such that the dosage form is retained in the stomach of a subject in a fed mode and the dose of acamprosate is released over an extended period of time.

In one embodiment, the acamprosate is acamprosate calcium. In another embodiment, the acamprosate is in a free acid form. In still another embodiment, another pharmaceutically acceptable salt of acamprosate is used, including magnesium, sodium or potassium.

In one embodiment, the gastric retained ER dosage form provides a mean AUC of plasma acamprosate in the subject which is greater than the mean AUC of plasma acamprosate provided by an immediate release (IR) acamprosate dosage form, wherein the dose of acamprosate in the ER dosage form is the same as or less than the dose in the IR dosage form. In another embodiment, the mean AUC of plasma acamprosate is about 10% to 50%, about 15% to about 30%, about 5% to 15%, about 5% to 20%, about 10% to 20%, about 10% to 25%, about 15% to 25%, about 20% to 25%, about 20% to 30%, about 20% to 40%, or about 30% to 40% greater than the AUC of plasma acamprosate provided by administration of the IR dosage form to the subject. In another embodiment, the mean. AUC of plasma acamprosate is about 5%, 10%, 15%, 20%, 25%, 30%, 35%, 40%, 45%, 50% or more than about 50% greater than the mean AUC of plasma acamprosate provided by administration of the IR dosage form to the subject.

In one embodiment, the gastric retained ER dosage form provides a mean Cmax of plasma acamprosate in the subject which is less than the mean Cmax of plasma acamprosate provided by an immediate release (IR) acamprosate dosage form, wherein the dose of acamprosate in the ER dosage form is the same as the dose in the IR dosage form. In another embodiment, the mean Cmax of plasma acamprosate is about 10% to 50%, about 15% to about 30%, about 5% to 15%, about 5% to 20%, about 10% to 20%, about 10% to 25%, about 15% to 25%, about 20% to 25%, about 20% to 30%, about 20% to 40%, or about 30% to 40% less than the Cmax of plasma acamprosate provided by administration of the IR dosage form to the subject. In another embodiment, the mean Cmax of plasma acamprosate is about 5%, 10%, 15%, 20%, 25%, 30%, 35%, 40%, 45%, 50% or more than about 50% less than the mean Cmax of plasma acamprosate provided by administration of the IR dosage form to the subject.

In one embodiment, the gastric retained ER dosage form provides a mean Tmax for plasma acamprosate in the subject who has been administered acamprosate in the ER dosage form as described herein is greater than the mean Tmax of plasma acamprosate provided by an immediate release (IR) acamprosate dosage form, wherein the dose of acamprosate in the ER dosage form is the same as the dose in the IR dosage form. In another embodiment, the mean Tmax for plasma acamprosate in the subject who has been administered acamprosate in the ER dosage form as described herein is about 2 hours (h) to 5 h, about 3 h to 5 h, about 4 h to 5 h, about 2 h to 6 h, about 3 h to 6 h, about 3 h to 5 h, about 3 h to 4 h, or about 4 h to 6 h.

In one embodiment, the oral dosage form is a tablet. In another embodiment, the total tablet weight is about 500 mg or about 1000 mg (milligrams). In still another embodiment, the total tablet weight is about 1200 mg. In yet another embodiment, the total tablet weight is about 500 mg to about 1500 mg, 750 mg to 1500 mg, 800 mg to 1300 mg, 900 mg to 1250 mg, or about 800 to 1200 mg.

In one embodiment, the tablet comprises a total of about 200 mg to about 1000 mg, or about 300 mg to about 750 mg acamprosate. In another embodiment, the tablet comprises about 300 mg to 850 mg, 350 mg to 800 mg, 400 mg to 700 mg, 450 mg, 550 mg, 600 mg, 650 mg, 700 mg, 750 mg, 800 mg, or 850 mg acamprosate. In yet another embodiment, the tablet comprises about 50 wt % (weight percent) or about 75 wt % acamprosate. In still another embodiment, the tablet comprises about 30 wt %, 35 wt %, 40 wt %, 45 wt %, 55 wt %, 60 wt %, 65 wt %, 70 wt %, 75 wt % or about 80 wt % acamprosate.

In one embodiment, the tablet comprises about 20 mg, 25 mg, 30 mg, 35 mg, 40 mg, 45 mg, or 50 mg of one or more binders. In another embodiment, the tablet comprises about 1 wt %, 2 wt %, 2.5 wt %, 3 wt %, 3.5 wt %, 4 wt %, 4.5 wt %, 5 wt %, or 6 wt % binder. In yet another embodiment, the tablet comprises about 1 wt % to about 6 wt % or about 2 wt % to about 5 wt % of a binder.

In one embodiment, the tablet comprises a binder which is polyvinylpyrrolidone, polyvinylalcohol, ethyl cellulose, hydroxypropylcellulose, hydroxypropylmethylcellulose, hydroxyethylcellulose or polyethylene glycol. In yet another embodiment, the polyvinylpyrrolidone is povidone, copovidone. In yet another embodiment, the tablet comprises a combination of more than one binder.

In one embodiment, the tablet comprises about 380 mg, 400 mg, 420 mg, 440 mg, 460 gm, 480 mg, 500 mg, 520 mg, 540 mg, 560 mg, 580 mg, 600 mg, or 620 mg of one or more hydrophilic polymers. In another embodiment, the tablet comprises about 15 wt % to about 50 wt %, about 20 wt % to about 75 wt %, about 25 wt % to about 60 wt %, about 30 wt % to about 45 wt %, about 25 wt % to about 40 wt %, or about 30 wt % to about 50 wt % of a hydrophilic polymer. In yet another embodiment, the tablet comprises about 15 wt %, 18 wt %, 20 wt %, 25 wt %, 28 wt %, 30 wt %, 32 wt %, 33 wt %, 35 wt %, 37 wt %, 40 wt %, 45 wt %, 50 wt %, 55 wt %, 60 wt %, 65 wt %, 70 wt %, 75 wt %, 80 wt %, 85 wt %, or 90 wt % of a hydrophilic polymer.

In one embodiment, the tablet comprises one or more hydrophilic polymers, each having an average molecular weight ranging from about 200,000 Da (Daltons) to about 10,000,000 Da, about 900,000 Da to about 5,000,000 Da, about 2,000,000 Da to about 5,000,000 Da, from about 4,000,000 Da to about 5,000,000 Da, from about 5,000,000 Da to about 7,000,000 Da, from about 2,000,000 Da to about 4,000,000 Da, from about 900,000 Da to about 5,000,000 Da, or from about 900,000 Da to about 4,000,000 Da. In another embodiment, the tablet comprises a hydrophilic polymer having an average molecular weight of about 200,000 Da, 600,000 Da, 900,000 Da, 1,000,000 Da, 2,000,000 Da, 4,000,000 Da, 5,000,000 Da, 7,000,000 Da, 10,000,000 Da or 12,000,000 Da. In still another embodiment, the hydrophillic polymer has a viscosity range from about 55 cp to 17,600 cp in a 5% solution at 25° C., from about 400 cp to 4,000 cp in a 2% solution at 25° C. or from about 1,650 cp to 10,000 cp in a 1% solution at 25° C.

In one embodiment, the ER layer comprises a hydrophilic polymer which is a cellulose-based or cellulose-derived polymer having an average viscosity ranging from about 4,000 cp (centipoise) to about 200,000 cp, from about 50,000 cp to about 200,000 cp, or from about 80,000 cp to about 120,000 cp as measured as a 2% weight per volume in water at 20° C.

In one embodiment, the ER layer comprises a hydrophilic polymer which is a cross-linked polyacrylic acid. In another embodiment, the polyacrylic acid has a viscosity range from about 4 to 40,000 cp for a 1% solution at 25° C.

In one embodiment, the one or more hydrophilic polymers in the tablet is a polyalkylene oxide. In another embodiment, the hydrophilic polymer is poly(ethylene oxide). In yet another embodiment, the at least one hydrophilic polymer in the tablet is a cellulose. In yet another embodiment, the cellulose is hydroxypropyl methylcellulose.

In one embodiment, the tablet comprises two hydrophilic polymers in a ratio of 1:1, 1.2:1, 1.3:1, 1.4:1, 1.5:1, 1.6:1, 1.8:1, or 2.0:1.

In one embodiment, the tablet comprises about 8 mg, 9 mg, 10 mg, 11 mg, 12 mg, 13 mg, 14 mg, or 15 mg of one or more lubricants. In another embodiment, the tablet comprises about 0.5 wt % to about 2.5 wt % of a lubricant. In yet another embodiment, the tablet comprises about 0.5 wt %, 1.0 wt %, 1.5 wt %, 2.0 wt %, or 2.5 wt % of a lubricant.

In one embodiment, the tablet comprises a lubricant which is magnesium stearate, calcium stearate, sodium stearyl fumarate, stearic acid, stearyl behenate, glyceryl behenate, or polyethylene glycol.

In one embodiment, the tablet comprises one or more additional excipients which are diluents, coloring agents, flavoring agents, and/or glidants.

In one embodiment, the dosage form is a single layer tablet. In another embodiment, the dosage form comprises a coat. In yet another embodiment, the coat comprises one or more active agents. In still another embodiment, the coat comprises the acamprosate.

In one embodiment, the dosage form comprises a coat which does not function as an enteric coating.

In one embodiment, the dosage form is a tablet which comprises enteric coated particles of acamprosate. In another embodiment, the enteric coat dissolves at a pH of less than about 7.0, 6.5, 6.0, 5.5 or 5.0. In still another embodiment, the enteric coat dissolves at a pH of about 5 to 6, or about 5.5 to 6.5.

In one embodiment, the dosage form is a bilayer or multi-layer tablet. In another embodiment, the dosage form comprises a layer which is a floating layer. In still another embodiment, the dosage form comprises a layer which is an IR layer.

In one embodiment, the dosage form is an osmotic dosage form.

In one embodiment, the dosage form comprises an immediate release matrix containing the acamprosate, surrounded by a rate-limiting membrane. In another embodiment, the rate-limiting membrane functions as a semi-permeable membrane when immersed in fluid.

In one embodiment, the dosage form comprises a second therapeutic agent. In another embodiment, the second therapeutic agent is naltrexone. In yet another embodiment, the second therapeutic agent is formulated for extended release or immediate release.

In one embodiment, the dosage form is formulated to provide sustained release of the acamprosate and the second therapeutic agent.

In one embodiment, the single layer, bilayer, multilayer tablet has a friability of no greater than about 0.1%, 0.2% 0.3%, 0.4%, 0.5%, 0.7% or 1.0%.

In one embodiment, the tablet has a hardness of at least about 10 kiloponds (kp). In some embodiments, the tablet has a hardness of about 9 kp to about 25 kp, or about 12 kp to about 20 kp. In further embodiments, the tablet has a hardness of about 11 kp, 12 kp, 13 kp, 14 kp, 15 kp, 16 kp, 17 kp, 18 kp, 19 kp, 20 kp, 21 kp, 22 kp, 23 kp, 24 kp or 25 kp.

In one embodiment, the tablets have a content uniformity of from about 85 to about 115 percent by weight or from about 90 to about 110 percent by weight, or from about 95 to about 105 percent by weight. In other embodiments, the content uniformity has a relative standard deviation (RSD) equal to or less than about 3.5%, 3.0%, 2.5%, 2.0%, 1.5%, 1.0% or 0.5%.

In one embodiment, at least 80% of the acamprosate is released from the tablet over a time period of about 5 to 13 h (hours), about 6 to 12 h, about 7 to 10 h, about 8 to 9 h, about 6 h to 9 h, about 8 to 10 h, or about 9 to 10 h. In another embodiment, the acamprosate is delivered to the small intestine of a subject over a time period of at least about 4 h, 5 h, 6 h, 7 h, 8 h, 9 h, 10 h, 11 h, 12 h, or 13 h.

In one embodiment, the acamprosate is in enteric coated particles or beads. In another embodiment, the acamprosate is released from the tablet via erosion. In another embodiment, the acamprosate, especially if it is not in enteric coated particles, is released from the tablet via diffusion. In yet another embodiment, the acamprosate is released from the tablet via a combination of erosion and diffusion.

In one embodiment, about 5% to about 20% of the dose of acamprosate in the ER portion of the dosage form is released within 10 minutes, 15 minutes, 30 minutes, 45 minutes or 60 minutes after oral administration.

In one embodiment, not more than about 15%, 20%, 30%, or 40% of the dose of acamprosate is released within about the first hour. In another embodiment, not more than about 25%, 30%, 35%, 40%, 45%, 50%, 55%, 60%, 65%, 70%, 75%, or 80% of the dose of acamprosate is released within about 4 hours.

In one embodiment, at least about 80% of the acamprosate in the ER portion of the dosage form is released from the dosage form after about 6 hours, 7 hours, 8 hours, 9 hours, 10 hours, 11 hours or 12 hours of administration.

In one embodiment, the tablet swells upon imbibition of fluid from gastric fluid to a size which is approximately 15%, 20%, 25%, 30%, 35% 40%, 45%, or 50% larger than the size of the tablet prior to imbibition of fluid. In other embodiments the tablet swells to a size that is 75%, 100%, 200%, 300% or even greater than the original size of the tablet.

In one embodiment, the dosage form provides a dissolution profile wherein between about 50% to about 85%, about 55% to about 80% or about 35% to about 55% of the dose of acamprosate remains in the tablet between about 1 and 2 hours after administration. In yet another embodiment, not less than about 50%, 55%, 60%, 65%, 70%, or 75% is released after about 6 hours. In yet another embodiment, not less than about 60% is released after about 6 hours.

In a second aspect, a method of making a gastric retentive dosage form comprising acamprosate and at least one hydrophilic polymer is provided. In one embodiment, the acamprosate is acamprosate calcium.

In one embodiment, a method of making the dosage form comprising wet granulating acamprosate with one or more binders and/or one or more disintegrants is provided, wherein granules are formed. In another embodiment, the method of making the dosage form further comprises screening the dry granules based on size. In yet another embodiment, the method of making the dosage form further comprises blending the granules with additional excipients.

In one embodiment, a gastric retained dosage form comprising acamprosate and at least one swellable polymer is administered to a subject suffering from or diagnosed with alcohol dependence.

In one embodiment, a gastric retained dosage form comprising acamprosate is administered to a subject in a fed mode. In another embodiment, the dosage form is administered with a meal to a subject once in a 24 hour period. Dinner may be the preferred meal. In other embodiments, the dosage form is administered with a meal to the subject twice or thrice in a 24 hour period. Breakfast and dinner may be the preferred meals for the twice daily dose. The dosage administered with the evening meal may or may not be greater than with the morning meal. In yet another embodiment, the dosage form is administered with a meal to a subject once or twice in a 24 hour period for 2, 3, 4, 5, 6, 7, 8 or more days.

In one aspect, a method of treatment comprises administering to a subject in need thereof a dose of acamprosate or a pharmaceutically acceptable salt thereof dispersed in a polymeric matrix wherein the polymeric matrix comprises one or more polymers that upon imbibition of fluid swells to a size sufficient to promote gastric retention, wherein upon administration to the subject, the gastric retentive dosage form provides a mean AUC of plasma acamprosate greater than the mean AUC of plasma acamprosate provided by an immediate release (IR) dosage form which contains a dose of acamprosate or pharmaceutically acceptable salt thereof equal to or more than the dose of acamprosate in the gastric retentive dosage form.

In one embodiment, the subject is administered a total daily dose of about 300 mg to about 2500 mg acamprosate. In another embodiment, the total daily dose is about 300 mg to about 2000 mg, about 500 mg to about 1500 mg, about 600 mg to about 1200 mg, or about 300 mg, 400 mg, 500 mg, 600 mg, 700 mg, 800 mg, 900 mg, 1000 mg, 1100 mg, 1200 mg, 1500 mg, 1600 mg, 1800 mg, 2000 mg, 2200 mg, or 2500 mg.

In one embodiment, the total daily dose is administered via a once-per-day regimen or via a twice-per-day regimen.

In a third aspect, a method for treating a subject suffering from alcohol dependence, tinnitus, sleep apnea, Parkinson's disease, levodopa-induced dyskinesias in Parkinson's disease, Alzheimer's disease, Huntington's disease, Amyotrophic lateral sclerosis, Cortical spreading depression, migraine, schizophrenia, anxiety, tardive dyskinesia, spasticity, multiple sclerosis, various types pain, or binge eating, comprising administering a gastric retained acamprosate oral dosage form is provided.

In one embodiment, the acamprosate is a free acid, acamprosate calcium, or another pharmaceutically acceptable salt of acamprosate.

In one embodiment, adverse side effects elicited by the administration of the acamprosate extended release dosage form are reduced at least about 10%, 15%, 25%, 30%, 40% or 50% as compared to administration of an equivalent dose of an immediate release formulation comprising acamprosate.

DETAILED DESCRIPTION

Figure 1:
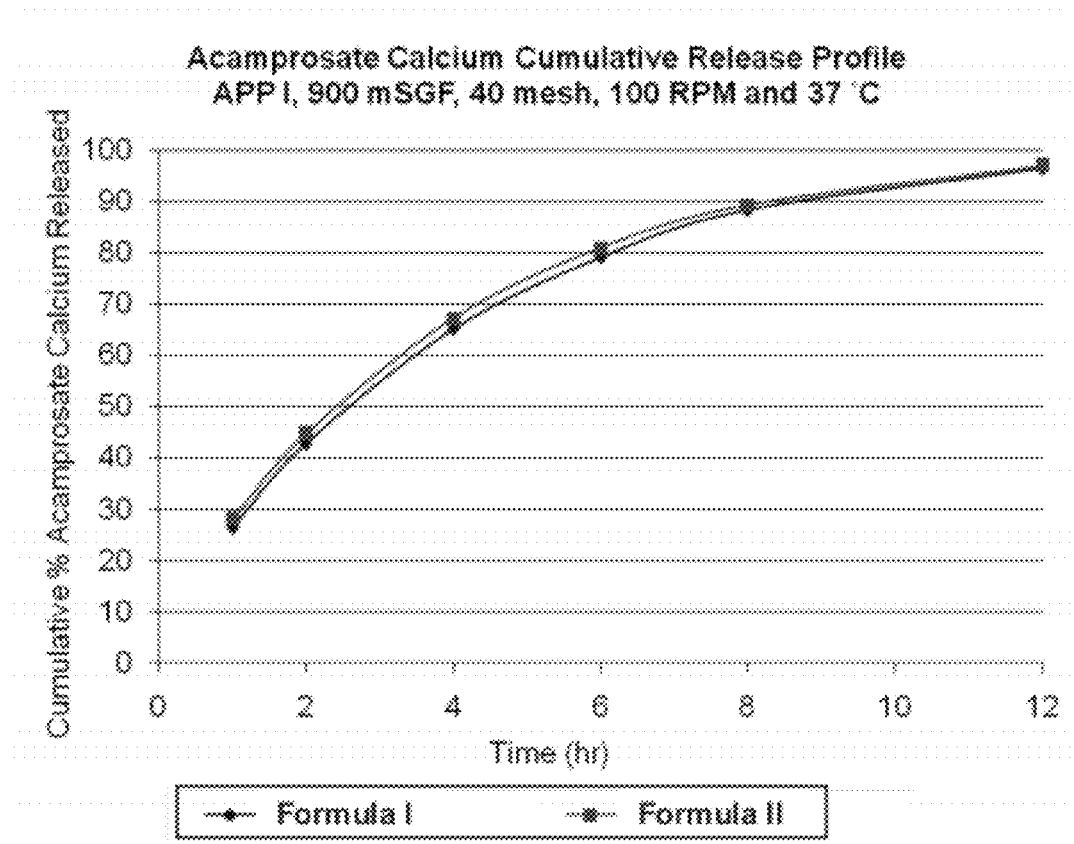
FIG. 1 is a graph showing release of acamproste calcium from extended release dosage forms.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art.

I. DEFINITIONS

It must be noted that, as used in this specification, the singular forms "a," "an," and "the" include plural referents unless the context clearly dictates otherwise.

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

"Optional" or "optionally," as used herein, means that the subsequently described element, component or circumstance may or may not occur, so that the description includes instances where the element, component, or circumstance occurs and instances where it does not.

The terms "subject," "individual" or "patient" are used interchangeably herein and refer to a vertebrate, preferably a mammal. Mammals include, but are not limited to, humans.

The term "about", particularly in reference to a given quantity, is meant to encompass deviations of plus or minus five percent.

The term "fed mode," as used herein, refers to a state which is typically induced in a patient by the presence of food in the stomach, the food-giving rise to two signals, one that is said to stem from stomach distension and the other a chemical signal based on food in the stomach. It has been determined that once the fed mode has been induced, larger particles are retained in the stomach for a longer period of time than smaller particles; thus, the fed mode is typically induced in a patient by the presence of food in the stomach. The fed mode is initiated by nutritive materials entering the stomach upon the ingestion of food. Initiation is accompanied by a rapid and profound change in the motor pattern of the upper GI tract, over a period of 30 seconds to one minute. The change is observed almost simultaneously at all sites along the G.I. tract and occurs before the stomach contents have reached the distal small intestine. Once the fed mode is established, the stomach generates 3-4 continuous and regular contractions per minute, similar to those of the fasting mode but with about a quarter to half the amplitude (Force). The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 8 hours or more. Administration of a dosage form "with a meal," as used herein, refers to administration during or after a meal. When the dosage form is administered after a meal, it may be administered about 1, 2, 3, 4, 5, 10, 15 minutes after completion of a meal.

A drug "release rate," as used herein, refers to the quantity of drug released from a dosage form or pharmaceutical composition per unit time, e.g., milligrams of drug released per hour (mg/hr). Drug release rates for drug dosage forms are typically measured as an in vitro rate of dissolution, i.e., a quantity of drug released from the dosage form or pharmaceutical composition per unit time measured under appropriate conditions and in a suitable fluid. Drug release tests may be obtained for the dosage forms or pharmaceutical compositions described herein using, for example, a USP Apparatus I (basket at 75 rmp, 100 rmp or 150 rpm), a USP Apparatus II (paddle at 50-100 rpm or 50 rpm, 75 rpm or 100 rpm), or a USP Dissolution Apparatus III (reciprocating cylinder) or a USP Disintegration tester. Tests are performed, for example, at about pH 1.2 (modified simulated gastric fluid, or mSFG), about pH 4.5 (the approximate pH of the stomach after a meal), about pH 6.8 or at about pH 7.5. Such testing may also be performed, for example, at about 37° C. or 25° C. Suitable aliquots of the release rate solutions are tested to determine the amount of drug released from the dosage form or pharmaceutical composition. For example, the drug can be assayed or injected into a chromatographic system to quantify the amounts of drug released during the testing intervals.

The terms "hydrophilic" and "hydrophobic" are generally defined in terms of a partition coefficient P, which is the ratio of the equilibrium concentration of a compound in an organic phase to that in an aqueous phase. A hydrophilic compound has a P value less than 1.0, typically less than about 0.5, where P is the partition coefficient of the compound between octanol and water, while hydrophobic compounds will generally have a P greater than about 1.0, typically greater than about 5.0. The polymeric carriers herein are hydrophilic, and thus compatible with aqueous fluids such as those present in the human body.

The term "polymer" as used herein refers to a molecule containing a plurality of covalently attached monomer units, and includes branched, dendrimeric, and star polymers as well as linear polymers. The term also includes both homopolymers and copolymers, e.g., random copolymers, block copolymers and graft copolymers, as well as uncrosslinked polymers and slightly to moderately to substantially crosslinked polymers, as well as two or more interpenetrating cross-linked networks.

The term "swellable polymer," as used herein, refers to a polymer that will swell in the presence of a fluid. It is understood that a given polymer may or may not swell when present in a defined drug formulation. Accordingly, the term "swellable polymer" defines a structural feature of a polymer which is dependent upon the composition in which the polymer is formulated. Whether or not a polymer swells in the presence of fluid will depend upon a variety of factors, including the specific type of polymer and the percentage of that polymer in a particular formulation. For example, the term "polyethylene oxide" or "PEO" refers to a polyethylene oxide polymer that has a wide range of molecular weights. PEO is a linear polymer of unsubstituted ethylene oxide and has a wide range of viscosity-average molecular weights. Examples of commercially available PEOs and their approximate molecular weights are: POLYOX® NF, grade WSR coagulant, approximate molecular weight 5 million, POLYOX® grade WSR 301, approximate molecular weight 4 million, POLYOX® grade WSR 303, approximate molecular weight 7 million, POLYOX® grade WSR N-60K, approximate molecular weight 2 million, and POLYOX® grade N-80K, approximate molecular weight 200,000. It will be understood by a person with ordinary skill in the art that an oral dosage form which comprises a swellable polymer will swell upon imbibition of water or fluid from gastric fluid.

The terms "swellable" and "bioerodible" (or simply "erodible") are used to refer to the polymers used in the present dosage forms, with "swellable" polymers being those that are capable of absorbing water and physically swelling as a result, with the extent to which a polymer can swell being determined by the molecular weight or degree of crosslinking (for crosslinked polymers), and "bioerodible" or "erodible" polymers referring to polymers that slowly dissolve and/or gradually hydrolyze in an aqueous fluid, and/or that physically disentangle or undergo chemical degradation of the chains themselves, as a result of movement within the stomach or GI tract.

The term "plasticizer" as used herein includes any compounds capable of plasticizing or softening a polymer or a binder used in the present invention. The use of plasticizers is optional, and can be included in the dosage form to modify the properties and characteristics of the polymers used in the coat(s) or core of the dosage form for convenient processing during manufacture of the coat(s) and/or the core of the dosage form. Once the coat(s) and/or core have been manufactured, certain plasticizers can function to increase the hydrophilicity of the coat(s) and/or the core of the dosage form in the environment of use. During manufacture of the coat(s) and/or core, the plasticizer can lower the melting temperature or glass transition temperature (softening point temperature) of the polymer or binder. Plasticizers can be included with a polymer and lower its glass transition temperature or softening point. Plasticizers also can reduce the viscosity of a polymer. Plasticizers can impart some particularly advantageous physical properties to the dosage forms of the invention. Examples of plasticizers include but are not limited to triethyl citrate, cetyl alcohol and mixtures of cetyl alcohol and triethyl citrate. Plasticizers may be present in the ER portion in an amount ranging from about 0.5 wt % to 5.0 wt %, about 1.0 wt % to about 3.0 wt % or about 2.0 wt % to about 3.0 wt %.

The term "friability," as used herein, refers to the ease with which a tablet will break or fracture. The test for friability is a standard test known to one skilled in the art. Friability is measured under standardized conditions by weighing out a certain number of tablets (generally 20 tablets or less), placing them in a rotating Plexiglas drum in which they are lifted during replicate revolutions by a radial lever, and then dropped approximately 8 inches. After replicate revolutions (typically 100 revolutions at 25 rpm), the tablets are reweighed and the percentage of formulation abraded or chipped is calculated. The friability of the tablets, of the present invention, is preferably in the range of about 0% to 3%, and values about 1%, or less, are considered acceptable for most drug and food tablet contexts. Friability which approaches 0% is particularly preferred.

The term "tap density" or "tapped density," as used herein, refers to a measure of the density of a powder. The tapped density of a pharmaceutical powder is determined using a tapped density tester, which is set to tap the powder at a fixed impact force and frequency. Tapped density by the USP method is determined by a linear progression of the number of taps.

The term "bulk density," as used herein, refers to a property of powders and is defined as the mass of many particles of the material divided by the total volume they occupy. The total volume includes particle volume, inter-particle void volume and internal pore volume.

The term "capping," as used herein, refers to the partial or complete separation of top or bottom crowns of the tablet main body. For multilayer tablets, capping refers to separation of a portion of an individual layer within the multilayer tablet. Unintended separation of layers within a multilayer tablet prior to administration is referred to herein as "splitting."

The term "content uniformity," as used herein refers to the testing of compressed tablets to provide an assessment of how uniformly the micronized or submicron active ingredient is dispersed in the powder mixture. Content uniformity is measured by use of USP Method (General Chapters, Uniformity of Dosage Forms), unless otherwise indicated. A plurality refers to five, ten or more tablet compositions.

The terms "effective amount" or a "therapeutically effective amount" refer to the amount of drug or pharmacologically active agent to provide the desired effect without toxic effects. The amount of an agent that is "effective" may vary from individual to individual, depending on the age, weight, general condition, and other factors of the individual. An appropriate "effective" amount in any individual may be determined by one of ordinary skill in the art using routine experimentation. An "effective amount" of an agent can refer to an amount that is either therapeutically effective or prophylactically effective or both.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. The term "pharmacologically active" (or simply "active") as in a "pharmacologically active" derivative, refers to a derivative having the same type of pharmacological activity as the parent compound and/or drug and approximately equivalent in degree. When the term "pharmaceutically acceptable" is used to refer to a derivative (e.g., a salt) of an active agent, it is to be understood that the compound is pharmacologically active as well. When the term, "pharmaceutically acceptable" is used to refer to an excipient, it implies that the excipient has met the required standards of toxicological and manufacturing testing or that it is on the Inactive Ingredient Guide prepared by the FDA, or comparable agency.

The terms "drug," "active agent," "therapeutic agent," and/or "pharmacologically active agent" are used interchangeably herein to refer to any chemical compound, complex or composition that is suitable for oral administration and that has a beneficial biological effect, preferably a therapeutic effect in the treatment or prevention of a disease or abnormal physiological condition. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "drug" are used, then, or when a particular active agent is specifically identified, it is to be understood that applicants intend to include the active agent per se as well as pharmaceutically acceptable, pharmacologically active salts, esters, amides, prodrugs, metabolites, analogs, etc.

The term "dosage form" refers to the physical formulation of the drug for administration to the patient. Dosage forms include without limitation, tablets, capsules, caplets, liquids, syrups, lotions, lozenges, aerosols, patches, enemas, oils, ointments, pastes, powders for reconstitution, sachets, solutions, sponges, and wipes. Within the context of the present invention, a dosage form comprising an acamprosate formulation will generally be administered to patients in the form of tablets.

The term "dosage unit" refers to a single unit of the dosage form that is to be administered to the patient. The dosage unit will be typically formulated to include an amount of drug sufficient to achieve a therapeutic effect with a single administration of the dosage unit although where the size of the dosage form is at issue, more than one dosage unit may be necessary to achieve the desired therapeutic effect. For example, a single dosage unit of a drug is typically, one tablet, one capsule, or one tablespoon of liquid. More than one dosage unit may be necessary to administer sufficient drug to achieve a therapeutic effect where the amount of drug causes physical constraints on the size of the dosage form.

"Delayed release" dosage forms are a category of modified release dosage forms in which the release of the drug is delayed after oral administration for a finite period of time after which release of the drug is unhindered. Delayed release dosage forms are frequently used to protect an acid-labile drug from the low pH of the stomach or where appropriate to target the GI tract for local effect while minimizing systemic exposure. Enteric coating is frequently used to manufacture delayed release dosage forms.

The terms "sustained release," and "extended release" are used interchangeably herein to refer to a dosage form that provides for gradual release of a drug over an extended period of time. With extended release dosage forms, the rate of release of the drug from the dosage form is reduced in order to maintain therapeutic activity of the drug for a longer period of time or to reduce any toxic effects associated with a particular dosing of the drug. Extended release dosage forms have the advantage of providing patients with a dosing regimen that allows for less frequent dosing, thus enhancing compliance. Extended release dosage forms can also reduce peak-related side effects associated with some drugs and can maintain therapeutic concentrations throughout the dosing period thus avoiding periods of insufficient therapeutic plasma concentrations between doses. Reference herein to a gastric retained extended release (ER) dosage form refers to a dosage form described herein which comprises an ER portion. In other words, a gastric retained extended release dosage form may comprise both an ER and an IR portion, or both an ER portion and a swelling portion, etc.

The term "modified release" refers to a dosage form that includes both delayed and extended release drug products. The manufacture of delayed, extended, and modified release dosage forms are known to ordinary skill in the art and include the formulation of the dosage forms with excipients or combinations of excipients necessary to produce the desired active agent release profile for the dosage form.

The "gastric retentive" oral dosage forms described herein are a type of extended release dosage form. Gastric retentive dosage forms are beneficial for the delivery of drugs with reduced absorption in the lower GI tract or for local treatment of diseases of the stomach or upper GI tract. For example, in certain embodiments of gastric retentive oral dosage forms of the present invention, the dosage form swells in the gastric cavity and is retained in the gastric cavity of a patient in the fed med so that the drug may be released for heightened therapeutic effect. See, Hou et al., Crit. Rev. Ther. Drug Carrier Syst. 20(6):459-497 (2003).

The term "enteric coat" as used herein is defined to mean a coating or barrier applied to a dosage form that can control the location in the digestive system where the active drug(s) is absorbed. For example, an enteric coating can be used to: (i) protect the drug from the destructive action of the enzymes or low pH environment of the stomach; (ii) prevent nausea or bleeding associated with the irritation of the gastric mucosa by the drug; and/or (iii) deliver the drug in an undiluted form in the intestine. Based on these criteria, in certain embodiments, the enteric coated dosage form can be regarded as a type of delayed release dosage form. They differ from sustained release dosage forms in that with sustained release dosage forms, the drug release is extended over a period of time to maintain therapeutic blood levels and to decrease the incidence of side effects caused by a rapid release; whereas, with enteric coatings, the primary objective is to confine the release of the drug to a predetermined region of the gastrointestinal tract. Enteric coatings work by presenting a surface that is substantially stable at acidic pH, but breaks down at higher pH to allow release of the drug in the intestine.

The term "reverse enteric coat" as used herein is defined to mean a coating or barrier applied to a dosage form that can control the location in the digestive system where the active drug(s) is absorbed. Reverse enteric coatings work by presenting a surface that is substantially stable at a pH above 5, but breaks down at a pH up to about 5, to allow release of the drug in gastric juices. As such, the drug is soluble, swellable and/or permeable in digestive fluids (e.g., pH of about 5), and is substantially insoluble and/or stable at a pH higher than 5.

The term "enteric polymer" as used herein is defined to mean a polymeric substance that when used in an enteric coat formulation, is substantially insoluble and/or substantially stable under acidic conditions exhibiting a pH of less than about 5 and which are substantially soluble or can decompose under conditions exhibiting a pH of about 5 or more. Non-limiting examples of such enteric polymers include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate, polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate and mixtures thereof. Enteric polymers can be used individually or in combination with other hydrophobic or hydrophilic polymers in an enteric coat, a normal release matrix core, a controlled release matrix core, and/or in a controlled release coat. Enteric polymers can be combined with other pharmaceutically acceptable excipients to either facilitate processing of a coat including the enteric polymer or to alter the functionality of the coat.

The in vivo "release rate" and in vivo "release profile" refer to the time it takes for the orally administered dosage form, or the active agent-containing layer of a bilayer or multilayer tablet (administered when the stomach is in the fed mode) or the content of the active ingredient to be reduced to 0-10%, preferably 0-5%, of its original size or level, as may be observed visually using NMR shift reagents or paramagnetic species, radio-opaque species or markers, or radiolabels, or determined mathematically, such as deconvolution, upon its plasma concentration profiles.

The term "AUC" (i.e., "area under the curve," "area under the concentration curve," or "area under the concentration-time curve") is a pharmacokinetic term used to refer a method of measurement of bioavailability or extent of absorption of a drug based on a plot of an individual or pool of individual's blood plasma concentrations sampled at frequent intervals; the AUC is directly proportional to the total amount of unaltered drug in the patient's blood plasma. For example, a linear curve for a plot of the AUC versus dose (i.e., straight ascending line) indicates that the drug is being released slowly into the blood stream and is providing a steady amount of drug to the patient; if the AUC versus dose is a linear relationship this generally represents optimal delivery of the drug into the patient's blood stream. By contrast, a non-linear (i.e. less than dose proportional) AUC versus dose curve indicates rapid release of drug such that some of the drug is not absorbed, or the drug is metabolized before entering the blood stream.

The term "Cmax" (i.e., "maximum concentration") is a pharmacokinetic term used to indicate the peak concentration of a particular drug in the blood plasma of a patient.

The term "Tmax" (i.e., "time of maximum concentration" or "time of Cmax") is a pharmacokinetic term used to indicate the time at which the Cmax is observed during the time course of a drug administration. As would be expected, a dosage form that would include an immediate release as well as a gastric retentive component would have a shorter Tmax and higher Cmax for an immediate release dosage form, but longer Tmax and lower Cmax for a purely gastric retentive dosage form.

"Preventing," in reference to a disorder or unwanted physiological event in a patient, refers specifically to inhibiting or significant reducing the occurrence of symptoms associated with the disorder and/or the underlying cause of the symptoms.

"Therapeutically effective amount," in reference to a therapeutic agent, refers to an amount that is effective to achieve a desired therapeutic result. Therapeutically effective amounts of a given agent will typically vary with respect to factors such as the type and severity of the disorder or disease being treated and the age, gender, weight and other factors of the patient.

"Treating," "treat," and "treatment" refer to reduction in severity and/or frequency of symptoms, elimination of symptoms and/or underlying cause, prevention of the occurrence of symptoms and/or their underlying cause, and improvement or remediation of damage.

II. GASTRIC RETENTIVE DOSAGE FORM FOR THE EXTENDED RELEASE OF ACAMPROSATE

The pharmaceutical compositions described herein, i.e., gastric retained dosage forms comprising acamprosate, provide extended or sustained release of the acamprosate to the upper gastrointestinal tract. The presently described dosage forms provide for extended release of the acamprosate in the stomach wherein the dosage forms are comprised of a polymer matrix that swells upon imbibition of fluid to a size sufficient for gastric retention. Thus, in formulating the dosage forms, it is desirable to provide the properties which simultaneously allow: a) an extent of swelling to provide gastric retention over an extended period, and b) a rate of swelling and erosion that allows release of the acamprosate over a time period of approximately 6 to 12 hours.

IIa. Acamprosate

An acamprosate calcium dosage form currently marketed in the United States is sold as Campral®. Each CAMPRAL tablet contains 333 mg acamprosate calcium, which is equivalent to 300 mg acamprosate. These tablets are formulated as immediate release tablets, with the recommended dose between 2 tablets, 3 times daily.

Acamprosate calcium is a synthetic compound with a chemical structure similar to that of the endogenous amino acid homotaurine, which is a structural analogue of the amino acid neurotransmitter γ-aminobutyric acid and the amino acid neuromodulator taurine. Acamprosate calcium is highly hydrophilic and is freely soluble in water. The calcium salt is almost completely dissociated (98%) in hydrophilic media and the acetyl homotaurinic acid is a strong, completely dissociated acid, which means that it has a strongly charged functional group. Accordingly, it is thought that the low oral bioavailability of acamprosate is due to its poor intestinal membrane permeability (see Zornoza et al., 2003, CNS Drug Reviews, 9:359-374; Chabenat et al., 1988, Meth. Find. Exp. Clin. Pharmacol., 10:311-317).

The absolute bioavailability of CAMPRAL after oral administration is about 11%, with steady-state peak plasma concentrations after dosing with 2×333 mg tablets 3 times daily averaging 350 ng/ml and occurring at 3-8 hours post-dose (see CAMPRAL product insert). Interestingly, coadministration of CAMPRAL with food decreases bioavailability as measured by $C_{max}$ and AUC, by approximately 42% and 23%, respectively.

Acamprosate has proven effective in treating alcohol dependence. Such treatment helps subjects suffering from alcohol dependence abstain from alcohol ingestion. As acamprosate is effective in helping subjects abstain from drinking alcohol only as long as the subjects has therapeutically effective amounts of acamprosate in their blood, it is very useful to have access to an extended release dosage form which requires fewer doses during a 24 hour period. More recent studies suggest that acamprosate may also prove effective in the treatment of other indications such as tinnitus, sleep apnea, levodopa-induced dyskinesias in Parkinson's disease, Alzheimer's disease, Huntington's disease, amyotrophic lateral sclerosis, cortical spreading depression, migraine, schizophrenia, anxiety disorders, motion disorders, tardive dyskinesia, spasticity, multiple sclerosis, various types pain, or binge eating.

Described herein are oral dosage forms that provide sustained release of acamprosate from a gastric retained dosage form into the stomach, allowing delivery of the acamprosate to the small intestine for at least 8-12 hours. This release profile allows continual bathing of the small intestine in acamprosate present at concentrations which are therapeutically effective.

Design of a gastric retentive dosage form comprising acamprosate or a therapeutically acceptable salt thereof is challenging for multiple reasons. First, as noted above, the bioavailability of acamprosate is known to decrease in the presence of food. Yet, gastric retentive dosage forms such as those described herein, rely on the use of food to induce the fed mode, thereby reducing the diameter of the pyloric sphincter and promoting retention of the swellable dosage form in the stomach. Accordingly, it becomes imperative to design the gastric retained dosage form to provide a release profile such that use of food to induce the fed mode does not interfere with achieving the desired pharmacokinetic profile.

Another complication is the presence of a sulphonic acid functional group on the acamprosate. This group imparts a negative charge which affects the ability of the drug to be released from the dosage form at a desired rate. It becomes important to include excipients which allow sufficient swelling of the dosage form to promote retention in the stomach over an extended period of time while also providing the steady and extended release of the acamprosate into stomach, thereby providing the continual exposure of the drug to the walls of the upper small intestine.

A gastric retained extended dosage form as described herein has the added benefit of reduced side effects as compared to an immediate release dosage form, e.g., CAMPRAL. Side effects (adverse events) shown to occur as a rate of at least 3% than placebo in a CAMPRAL treatment group include accidental injury, asthenia, pain, anorexia, diarrhea, flatulence, nausea, anxiety, depression, dizziness, dry mouth, insomnia, paresthesia, pruritus, and sweating (see CAMPRAL prescribing information). In one embodiment, administration of the extended release gastric retained acamprosate dosage form described herein results in less than 3% of the patients experiencing one or more of the adverse events as compared to patients receiving placebo in a controlled clinical trial, wherein the adverse event is accidental injury, asthenia, pain, anorexia, diarrhea, flatulence, nausea, anxiety, depression, dizziness, dry mouth, insomnia, paresthesia, pruritus, and/or sweating. In another embodiment, the reduced side effect obverved with administration of the gastric retained ER dosage form is Moreover, the formulation of these pharmaceutical oral dosage forms must result in final products that meet the requirements of regulatory agencies such as the Food and Drug Administration. For example, final products must have a stable product that does not fracture during storage and transport. This is measured for tablets, in part, in terms of friability and hardness. Dosage forms must also meet the requirements for content uniformity, which essentially means that the dispersion of the active ingredient(s) is uniform throughout the mixture used to make the dosage form, such that the composition of tablets formed from a particular formulation does not vary significantly from one tablet to another. The FDA generally requires a content uniformity within a range of 95% to 105%.

The dosage form as described here may comprise one or more swellable polymers and are capable of swelling dimensionally unrestrained in the stomach upon contact with gastric fluid due to the component hydrophilic polymers, for example, polyethylene oxide and/or hypromellose (also known as hydroxypropyl methylcellulose or HPMC), and increase to a size sufficient to be retained in the stomach in a fed mode.

Water-swellable polymers suitable for use herein are those that swell in a dimensionally unrestrained manner upon contact with water Such polymers may also gradually erode over time. Examples of such polymers include polyalkylene oxides, such as polyethylene glycols, particularly high molecular weight polyethylene glycols; cellulose polymers and their derivatives including, but not limited to, hydroxyalkyl celluloses, hydroxymethyl cellulose, hydroxyethyl cellulose, hydroxypropyl cellulose, hydroxypropylmethyl cellulose, carboxymethylcellulose, microcrystalline cellulose; polysaccharides and their derivatives; chitosan; poly(vinyl alcohol); xanthan gum; maleic anhydride copolymers; poly (vinyl pyrrolidone); starch and starch-based polymers; maltodextrins; poly (2-ethyl-2-oxazoline); poly(ethyleneimine); polyurethane; hydrogels; crosslinked polyacrylic acids; and combinations or blends of any of the foregoing.

Further examples are copolymers, including block copolymers and graft polymers. Specific examples of copolymers are PLURONIC® and TECTONIC®, which are polyethylene oxide-polypropylene oxide block copolymers available from BASF Corporation, Chemicals Div., Wyandotte, Mich., USA. Further examples are hydrolyzed starch polyacrylonitrile graft copolymers, commonly known as "Super Slurper" and available from Illinois Corn Growers Association, Bloomington, Ill., USA.

Preferred swellable, erodible hydrophilic polymers suitable for forming the gastric retentive portion of the dosage forms described herein are poly(ethylene oxide), hydroxypropyl methyl cellulose, and combinations of poly(ethylene oxide) and hydroxypropyl methyl cellulose. Poly(ethylene oxide) is used herein to refer to a linear polymer of unsubstituted ethylene oxide. The molecular weight of the poly(ethylene oxide) polymers can range from about $9 \times 10^5$ Daltons to about $8 \times 10^6$ Daltons. Exemplary molecular weight poly(ethylene oxide) polymers include about $9 \times 10^5$ Daltons (e.g., SENTRY™ POLYOX™ WSR 1105, NF Grade, Dow Chemical), $2 \times 10^6$ Daltons (e.g., SENTRY™ POLYOX™ WSR N60K, NF Grade, Dow Chemical), $2 \times 10^6$ Daltons (e.g., SENTRY™ POLYOX™ WSR 301, NF Grade, Dow Chemical), and $7 \times 10^6$ Daltons (e.g., SENTRY™ POLYOX™ WSR N60K, NF Grade, Dow Chemical). The viscosity of a 1% water solution of the polymer at 25° C. preferably ranges from 4500 to 7500 centipoise.

Dosage forms prepared for oral administration according to the present disclosure will generally contain other inactive additives (excipients) such as binders, lubricants, disintegrants, fillers, stabilizers, surfactants, coloring agents, and the like.

Binders are used to impart cohesive qualities to a tablet, and thus ensure that the tablet or tablet layer remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Examples of polyvinylpyrrolidone include povidone, copovidone and crospovidone.

Lubricants are used to facilitate tablet manufacture, promoting powder flow and preventing particle capping (i.e., particle breakage) when pressure is relieved. Useful lubricants are magnesium stearate (in a concentration of from 0.25 wt % to 3 wt %, 0.2 wt % to 1.5 wt %, or about 1.0 wt %), calcium stearate, stearic acid, and hydrogenated vegetable oil (e.g., comprised of hydrogenated and refined triglycerides of stearic and palmitic acids at about 1 wt % to 5 wt % or less than about 2 wt %). Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Fillers include, for example, materials such as silicon dioxide, titanium dioxide, alumina, talc, kaolin, powdered cellulose, and microcrystalline cellulose, as well as soluble materials such as mannitol, urea, sucrose, lactose, lactose monohydrate, dextrose, sodium chloride, and sorbitol. Solubility-enhancers, including solubilizers per se, emulsifiers, and complexing agents (e.g., cyclodextrins), may also be advantageously included in the present formulations. Stabilizers, as well known in the art, are used to inhibit or retard drug decomposition reactions that include, by way of example, oxidative reactions.

In other embodiments, the excipients of the presently described dosage forms include one or more excipients which carry a charge opposite that of the acamprosate for pharmaceutically acceptable salt thereof. In some embodiments, the charged excipient is positively charged. As an example, a cationic excipient may include a polymeric quaternary ammonium compound. Other cationic polymers may include chitosan or a derivative thereof including, for example, trimethylchitosan and quarternised chitosan, and chitosan-derived materials including, for example, those taught in U.S. Pat. No. 5,747,475. Either high or low molecular weight chitosan products can be used in the pharmaceutical formulations of the present invention and are readily available in pharmaceutical grade from suppliers located world-wide. It is envisioned that release of the charged acamprosate may be further slowed via ionic interactions with one or more oppositely charged excipients.

Also envisioned is incorporation of the acamprosate or pharmaceutically acceptable salt thereof into the polymer matrix using hot-melt extrusion (HME) (see Vervaet et al., 2008, DOSIS, 24:119-123). HME allows the continuity of the hot-stage extrusion technique as the different process steps (mixing, melting, homogenizing and shaping) are carried out on a signle machine. This facilitates the production of matrices with excellent homogeneity. Polymers which can be processed via HME to function as part of a release-controlling matrix include but are not limited to synthetic cellulose derivatives (e.g., ethyl cellulose, hydroxypropylmethyl cellulose, cellulose-acetobutyrate), methacrylates, polyethylene oxides, polyvinylacetate, poly(lactide-co-glycolide), starch, lipids, and waxes. HME may also include combining the polymer with a plasticizer to optimze the thermoplastic properties of the polymer.

In one embodiment, a hot-melt process is performed in which the cationic polymer Eudragit RS (or RL) PO is melted together with the acamprosate calcium. The inoic interactions between the sulfonic acid group on the acamprosate and the quartinary amino of the Eudragit may slow release of the acamprosate from the tablet, as during the melt process the acamprosate and polymer are miscible. A hot melt process including a high molecular weight rate-controlling polymer such as POLYOX 303, in the presence of the acamprosate and/or other insoluble excipients, may results in a dosage form in which the rate of water penetration is further slowed, thereby slowing the rate of acamprosate release from the dosage form.

The gastric retentive dosage form may be a single layer, bilayer, or multilayer tablet or it may be a capsule. Multilayer tablets include tablets having a shell-and-core configuration in which a core is fully encased by a shell. Tablets may also have a coating with or without the pharmaceutically active agent. The tablet comprises a gastric retentive layer which comprises acamprosate or acamprosate calcium dispersed in a matrix comprised of at least one hydrophilic polymer which swells upon imbibition of fluid.

In one embodiment, a dosage form is formulated to have a dual-matrix configuration ("shell-and-core") as described in US publication US 2003/0104062 (herein incorporated by reference). One matrix forms a core of polymeric material in which the acamprosate or acamprosate calcium is dispersed and the other matrix forms a casing that surrounds and fully encases the core, the casing being of polymeric material that swells upon imbibition of water (and hence gastric fluid) to a size large enough to promote retention in the stomach during the fed mode, the shell and core being configured such that the drug contained in the core is released from the dosage form by diffusion through the shell. The shell is sufficient thickness and strength that it is not disrupted by the swelling and remains intact during substantially the entire period of drug release. The shell may or may not contain the acamprosate.

Water-swellable polymers useful in the preparation of the shell-and-core dosage form include polymers that are non-toxic and, at least in the case of the shell, polymers that swell in a dimensionally unrestricted manner upon imbibition of water. The core polymer may also be a swelling polymer, and if so, compatible polymers will be selected that will swell together without disrupting the integrity of the shell. The core and shell polymers may be the same or different, and if the same, they may vary in molecular weight, crosslinking density, copolymer ratio, or any other parameter that affects the swelling rate, so long as any swelling occurring in the core causes substantially not splitting of the shell.

In one embodiment, a tablet having an immediate release layer encased by an extended release gastric retained layer as a shell is manufactured.

In one embodiment, a tablet is formulated to have an extended release gastric retained (GR) layer spray-coated with an immediate release (IR layer) to provide 12-hour release of the acamprosate. In a further embodiment, the tablet contains 750 mg acamprosate, with 75 mg, 100 mg, 125 mg, or 150 mg acamprosate in the IR layer and 675 mg, 650 mg, 625 mg, or 600 mg acamprosate, respectively, in the GR layer.

In one embodiment, an oral dosage form is formulated as a pulsatile release dosage form, as described in U.S. Patent Publication No. 2009/028941 (incorporated herein by reference). In this embodiment, the oral dosage form may be comprised of: 1) a plurality of immediate release, enteric coated beads containing acamprosate, dispersed in a hydrophilic polymer that swells unrestrained dimensionally in water; 2) a series of inserts, each containing a plurality of immediate release beads containing the acamprosate, and each comprised of a swellable hydrophilic polymeric matrix, wherein the inserts are stacked to provide pulses of acamprosate over an extended period of time; and 3) a swellable hydrophilic matrix comprised of two or more regions, each region containing a dose of acamprosate, wherein the regions vary in size and position within the matrix to effect pulsed release of the acamprosate over an extended period of time.

In another embodiment, the gastric retained dosage form is a floating dosage form. Floatation of drug delivery systems as a gastroretentive mechanism has been widely used. These systems, also known as hydro-dynamically balanced, are buoyant on the gastric fluid and delay their emptying through the pyloric sphincter by swelling and expanding. Several approaches are currently used to prolong gastric retention time. These include floating drug delivery systems, also known as hydrodynamically balanced systems, swelling and expanding systems, polymeric bioadhesive systems, modified-shape systems, high-density systems, and other delayed gastric emptying systems. For example, Dave et al. (2004, AAPS PharmSciTech; 5:1-6) report on a gastroretentive drug delivery system of ranitidine hydrochloride using the principles of buoyant preparation, wherein guar gum, xanthan gum, and hydroxypropyl methylcellulose were evaluated for gel-forming properties, sodium bicarbonate was used as a gas-generating agent, and the effects of citric acid and stearic acid on drug release profile and floating properties were investigated. Similarly, Narendra et al. (2006, AAPS PharmSciTech, 7:E1-7) report on the development of an optimized gastric floating drug delivery system containing metoprolol tartrate as a model drug, wherein the dosage form was prepared as a bilayer tablet comprising a drug-loading layer and a floating layer in a suitable ratio to provide a bulk density lower than that of gastric fluids to remain buoyant on the stomach contents. Buoyancy is a result of a reduction in matrix density. Floatable delivery systems have been designed as single and multiple-unit devices.

Gastric retained extended release dosage forms may also be formulated as osmotic dosage forms such as an elementary osmotic dosage form or a push-pull osmotic pump. For example, U.S. Pat. Nos. 3,845,770 and 3,916,899 issued to Theeuwes and Higuchi pertains to an osmotic dosage form for delivering various drugs to a patient environment of use. The dosage forms disclosed in these patents are manufactured comprising a wall that surrounds a compartment comprising a drug with an exit in the wall for delivering the drug to a patient. In U.S. Pat. Nos. 4,008,719; 4,014,334; 4,058,122; 4,116,241; and 4,160,452 patentees Theeuwes and Ayer made available dosage forms comprising an inside and an outside wall made of poly(cellulose acylate) for delivering a dosage of drug to a patient in need thereof.

U.S. Pat. No. 6,245,357 describes osmotic dosage forms comprising a drug compartment and a pharmaceutically acceptable polymer hydrogel (maltodextrin, polyalkylene oxide, polyethylene oxide, carboxyalkylcellulose), contained within a bilayer interior wall and exterior wall and having a passageway, where the polymer exhibits an osmotic pressure gradient across the bilayer interior wall and exterior wall thereby imbibing fluid into the drug compartment to form a solution or a suspension comprising the drug that is hydrodynamically and osmotically delivered through a passageway from the dosage form. In certain embodiments, the dosage form further comprises a push displacement layer which expands to expel the drug from the dosage form. This patent describes that the interior wall of these dosage forms comprises a pore former which provides for increased permeability of the dosage form to water to compensate for the decrease in osmotic driving force that occurs as the osmagent and/or drug dissolves and is released from the dosage form. The dosage form was reported to exhibit a slow drug delivery until the osmotically-sensitive pore former dissolved or was leached from the inner wall. The eluted pore former caused the permeability of the inner wall to increase, which correspondingly caused the net permeability of the bilaminated inner wall-outer wall to increase over time. This increase in permeability was reported to offset any decrease in osmotic activity and produced a linear drug delivery profile. In addition, this patent describes dosage forms suitable for administering analgesic agents having a drug compartment comprising an opioid analgesic and a nonopioid analgesic and a polymer hydrogel, coated with an interior wall containing a pore former and an exterior wall.

Various devices and methods have been described having intended utility with respect to applications with high drug loading. For example, U.S. Pat. Nos. 4,892,778 and 4,940,465 describe dispensers for delivering a beneficial agent to an environment of use that include a semipermeable wall defining a compartment containing a layer of expandable material that pushes a drug layer out of the compartment formed by the wall. The exit orifice in the device is substantially the same diameter as the inner diameter of the compartment formed by the wall. Additionally, U.S. Pat. No. 6,368,626 describes high drug loading dosage forms for providing controlled release of active agents. This patent describes that the active agent is uniformly released from the dosage forms over a prolonged period of time, and that the release of the active agent from a dosage form does not vary positively or negatively by more than 30% from the mean rate of release of the active agent over a prolonged period of time, as determined in a USP Type 7 Interval Release Apparatus.

In one embodiment, one means for releasing the acamprosate from the dosage form includes a means for generating gas, which means for generating gas is surrounded by, for example, a semipermeable membrane. In operation, when the gas generating means imbibes water and/or aqueous biological fluids, the means for generating gas reacts and generates gas, thereby enlarging and expanding the at least one means for forcibly dispensing the tetrabenazine unidirectionally or multidirectionally. The means for generating a gas includes any compound or compounds, which can produce effervescence, such as for example, at least one solid acid compound and at least one solid basic compound, which in the presence of a fluid can react to form a gas, such as for example, carbon dioxide. Examples of acid compounds include, organic acids such as malic, fumaric, tartaric, itaconic, maleic, citric, adipic, succinic and mesaconic, and inorganic acids such as sulfamic or phosphoric, also acid salts such as monosodium citrate, potassium acid tartrate and potassium bitartrate. The basic compounds include, for example, metal carbonates and bicarbonates salts, such as alkali metal carbonates and bicarbonates. The acid and base materials can be used in any convenient proportion from about 1 to about 200 parts of the at least one acid compound to the at least one basic compound or from about 1 to about 200 parts of the at least one basic compound to the at least one acid compound. The means for generating gas is known.

In one embodiment, the gastric retained dosage form of acamprosate is a capsule dosage form that allows for the extended release of acamprosate in the stomach and comprises: (a) at least one component that expands on contact with gastric juice and contains an agent capable of releasing carbon dioxide or nitrogen, acamprosate or a pharmaceutically acceptable salt thereof; (b) at least one hydrophilic membrane in the form of a sachet which contains component (a), expands by inflation, floats on the aqueous phase in the stomach and is permeable to gastric juice and; (c) capsule dosage form which contains components (a) and (b) and which disintegrates without delay in the stomach under the action of gastric juice. Component (a) may also contain a pharmaceutically acceptable hydrophilic swelling agent such as lower alkyl ethers of cellulose, starches, water-soluble aliphatic or cyclic poly-N-vinylamides, polyvinyl alcohols, polyacrylates, polymethacrylates, polyethylene glycols and mixtures thereof, as well as other materials used in the manufacture of pharmaceutical dosage forms. Further details regarding an example of this type of dosage form can be found in Sinnreich, U.S. Pat. No. 4,996,058.

Dosage forms described herein can contain other materials that modify the physical form of the dosage, for example, as coatings. Thus, dosage forms, for example drug particles dispersed in a swellable hydrophilic matrix, can be coated with sugar, shellac, sustained and other enteric coating agents. Materials used in preparing these compositions should be pharmaceutically pure and nontoxic in the amounts used. Enteric coatings are well known in the art and can be selected for use based on the pH at which the enteric coating will dissolve in the gastrointestinal tract. The enteric coating is insoluble in a strongly acidic environment, such as the stomach, and releases the active agent in a more basic or less acidic environment, such as small intestine. This protects the active agent from degradation and provides a stable formulation.

The gastric retained dosage forms described herein are designed to provide release of acamprosate or a pharmaceutically acceptable salt thereof, to provide a pharmacokinetic profile which optimizes effective treatment of a subject suffering from, for example, alcohol dependence, tinnitus, sleep apnea, levodopa-induced dyskinesias in Parkinson's disease, Alzheimer's disease, Huntington's disease, amyotrophic lateral sclerosis, cortical spreading depression, migraine, schizophrenia, anxiety disorders, motion disorders, tardive dyskinesia, spasticity, multiple sclerosis, various types pain, or binge eating.

As seen in the examples below, a gastric retained extended release dosage form may provide bioavailability of the acamprosate such that an $AUC_{0-t}$ of from about 20,000 ng·h/ml to about 60,000 ng·h/ml, from about 30,000 ng·h/ml to about 50,000 ng·h/ml, or from about 40,000 ng·h/ml to about 45,000 ng·h/ml is achieved. Importantly, the Tmax is shifted as compared to the Tmax achieved upon administration of an IR dosage form. For example, the Tmax achieved by administering a gastric retained extended release dosage form comprising acamprosate may occur between about 2 h to 10 h, about 3 h to about 8 h, between about 4 h to about 7 h, or between about 5 h to about 6 h. The Cmax achieved by dosing of the subject with the gastric retained extended release acamprosate dosage form may range from about 1000 ng/ml to about 10,000 ng/ml, about 2000 ng/ml to about 8000 ng/ml, about 3000 ng/ml to about 6000 ng/ml or from about 4000 ng/ml to about 5500 ng/ml.

III. METHODS FOR MAKING THE DOSAGE FORMS

The presently described dosage forms provide for extended release of acamprosate in the stomach wherein the dosage forms are comprised of a polymer matrix that swells upon imbibition of fluid to a size sufficient for gastric retention. Thus, in formulating the dosage forms, it is desirable to provide the properties which simultaneously allow: a) an extent of swelling to provide gastric retention over an extended period, and b) a rate of swelling and erosion that allows release of the acamprosate over a time period of approximately 6 hours to 14 hours, and preferable 8 hours to 12 hours.

Moreover, the formulation of these pharmaceutical oral dosage forms preferably result in final products that meet the requirements of regulatory agencies such as the Food and Drug Administration. For example, final products desirably have a stable product that does not fracture during storage and transport. This is measured for tablets, in part, in terms of friability and hardness. Dosage forms preferably also satisfy requirements for content uniformity, which essentially means that the dispersion of the active ingredient(s) is uniform throughout the mixture used to make the dosage form, such that the composition of tablets formed from a particular formulation does not vary significantly from one tablet to another. The FDA requires a content uniformity within a range of 95% to 105%.

The ability to formulate a pharmaceutical oral dosage form which both delivers the therapeutically effective ingredient over a desired period of time and meets FDA requirements depends, in part and in some embodiments, upon the process by which the product is made.

In the case of gastric retentive tablets containing acamprosate, as disclosed herein, tablets may be made through direct compression or following a granulation procedure. Direct compression is used with a group of ingredients that can be blended, placed onto a tablet press, and made into a perfect tablet without any of the ingredients having to be changed. Powders that can be blended and compressed are commonly referred to as directly compressible or as direct-blend formulations. When powders do not compress correctly, a granulation technique is considered.

Granulation is a manufacturing process which increases the size and homogeneity of active pharmaceutical ingredients and excipients which comprise a solid dose formulation. The granulation process, which is often referred to as agglomeration, changes physical characteristics of the dry formulation, with the aim of improving manufacturability, and therefore, product quality.

Granulation technology can be classified into one of two basic types: wet granulation and dry granulation. Wet granulation is by far the more prevalent agglomeration process utilized within the pharmaceutical industry. Most wet granulation procedures follow some basic steps; the drug(s) and excipients are mixed together, and a binder solution is prepared and added to the powder mixture to form a wet mass. The moist particles are then dried and sized by milling or by screening through a sieve. In some cases, the wet granulation is "wet milled" or sized through screens before the drying step. There are four basic types of wet granulation; high shear granulation, fluid bed granulation, extrusion and spheronization and spray drying.

A. Dry Granulation

The dry granulation process involves three basic steps; the drug(s) and excipients(s) are mixed (along with a suitable binder if needed) and some form of lubrication, the powder mixture is compressed into dry "compacts," and then the compacts are sized by a milling step. The two methods by which dry granulation can be accomplished are slugging and roller compaction.

B. Fluid Bed (Wet) Granulation

The fluid bed granulation process involves the suspension of particulates within an air stream while a granulation solution is sprayed down onto the fluidized bed. During the process, the particles are gradually wetted as they pass through the spay zone, where they become tacky as a result of the moisture and the presence of binder within the spray solution. These wetted particles come into contact with, and adhere to, other wetted particles resulting in the formation of particles.

A fluid bed granulator consists of a product container into which the dry powders are charged, an expansion chamber which sits directly on top of the product container, a spray gun assembly, which protrudes through the expansion chamber and is directed down onto the product bed, and air handling equipment positioned upstream and downstream from the processing chamber.

The fluidized bed is maintained by a downstream blower which creates negative pressure within the product container/expansion chamber by pulling air through the system. Upstream, the air is "pre-conditioned" to target values for humidity, temperature and dew point, while special product retention screens and filters keep the powder within the fluid bed system.

As the air is drawn through the product retention screen it "lifts" the powder out of the product container and into the expansion chamber. Since the diameter of the expansion chamber is greater than that of the product container, the air velocity becomes lower within the expansion chamber. This design allows for a higher velocity of air to fluidize the powder bed causing the material to enter the spray zone where granulation occurs before loosing velocity and falling back down into the product container. This cycle continues throughout the granulation process.

The fluid bed granulation process can be characterized as having three distinct phases; pre-conditioning, granulation and drying. In the initial phase, the process air is pre-conditioned to achieve target values for temperature and humidity, while by-passing the product container altogether. Once desired or optimal conditions are met, the process air is re-directed to flow through the product container, and the process air volume is adjusted to a level which will maintain sufficient fluidization of the powder bed. This pre-conditioning phase completes when the product bed temperature is within the target range specified for the process.

In the next phase of the process, the spraying of the granulating solution begins. The spray rate is set to a fall within a pre-determined range, and the process continues until all of the solution has been sprayed into the batch. It is in this phase where the actual granulation, or agglomeration, takes place.

Once the binder solution is exhausted, the product continues to be fluidized with warm process air until the desired end-point for moisture content is reached. This end-point often correlates well with product bed temperature, therefore in a manufacturing environment, the process can usually be terminated once the target product bed temperature is reached. A typical fluid bed process may require only about thirty to forty-five minutes for the granulation step, plus ten to fifteen minutes on either side for pre-conditioning and drying.

As with any of the wet granulation processes, a variable is the amount of moisture required to achieve successful agglomeration. The fluid bed granulation process preferably provides a "thermodynamic" balance between process air temperature, process air humidity, process air volume and granulation spray rate. While higher process air temperature and process air volume add more heat to the system and remove moisture, more granulating solution and a higher solution spray rate add moisture and remove heat via evaporative cooling. These are process parameters which are preferably evaluated as a manufacturing process is developed, and a key to understanding the interdependency of each variable.

Additional factors affecting the outcome of the fluid bed granulation process are the amount and type of binder solution, and the method by which the binder is incorporated within the granulation. Other process variables are the total amount of moisture added through the process, and the rate at which the moisture content is increased. These parameters can have an effect on the quality and the characteristics of the granulation. For instance, a wetter fluid bed granulation process tends to result in a stronger granule with a higher bulk density. However, an overly aggressive process, where moisture is added too rapidly, can loose control over achieving the final particle size and particle size distribution objectives.

C. High Shear Granulation

Most pharmaceutical products manufactured by wet granulation utilize a high shear process, where blending and wet massing are accomplished by the mechanical energy generated by an impeller and a chopper. Mixing, densification and agglomeration are achieved through the "shear" forces exerted by the impeller; hence the process is referred to as high shear granulation.

The process begins by adding the dry powders of the formulation to the high shear granulator, which is a sealed "mixing bowl" with an impellor which rotates through the powder bed, and a chopper blade which breaks up over-agglomerates which can form during the process. There are typically three phases to the high shear process; dry mixing, solution addition, or wet massing and high shear granulation.

In the first phase, dry powders are mixed together by the impeller blade which rotates through the powder bed. The impeller blade is positioned just off the bottom of the product container. There is a similar tolerance between the tips of the impeller blade and the sides of the container. The impeller blades rotation trough the powder bed creates a "roping" vortex of powder movement. The dry mixing phase typically lasts for only a few minutes.

In the second phase of the process, a granulating liquid is added to the sealed product container, usually by use of a peristaltic pump. The solution most often contains a binder with sufficient viscosity to cause the wet massed particles to stick together or agglomerate. It is common for the solution addition phase to last over a period of from three to five minutes. While the impeller is rotating rather slowly during this step of the process, the chopper blade is turning at a fairly high rate of speed, and is positioned within the product container to chop up over-sized agglomerates, while not interfering with the impellers movement.

Once the binder solution has been added to the product container, the final stage of the granulation process begins. In this phase, high shear forces are generated as the impeller blades push through the wet massed powder bed, further distributing the binder and intimately mixing the ingredients contained therein. The impeller and chopper tool continue to rotate until the process is discontinued when the desired granule particle size and density end-points are reached. This end-point is often determined by the power consumption and/or torque on the impeller.

Once the high shear granulation process has been completed, the material is transferred to a fluid bed dryer, or alternatively, spread out onto trays which are then placed in a drying oven, where the product is dried until the desired moisture content is achieved, usually on the order of 1-2% as measured by Loss On Drying technique.

A variable which affects the high shear process is the amount of moisture required to achieve a successful granulation. A key to the process is having the right amount of moisture to allow for agglomeration to occur. Too little moisture will result in an under-granulated batch, with weak bonds between particles and smaller, to non-existent particles, with properties similar to those of the dry powder starting materials. On the other hand, excess moisture can result in a "crashed" batch with results varying from severe over-agglomeration to a batch which appears more like soup.

Other formulation parameters affecting the outcome of the high shear granulation process are the amount and type of binder solution, and the method by which the binder is incorporated within the granulation. For example, it is possible to include some of the binder in the dry powder mixture as well as in the granulating solution, or it may be incorporated only in the granulating solution or only in the dry powder, as is the case where water is used as the granulating solution.

The high shear granulation process parameters which are variable include impeller and chopper speeds, the solution addition rate, and the amount of time allocated to the various phases of the process. Of these, variables for consideration are the solution addition rate and the amount of time the wet massed product is under high shear mixing D. Extrusion and Spheronization This specialized wet granulation technique involves multiple processing steps and was developed to produce very uniform, spherical particles ideally suited for multi-particulate drug delivery of delayed and sustained release dosage forms.

Similar to high shear granulation initially, the first step involves the mixing and wet massing of the formulation. Once this step is complete, the wet particles are transferred to an extruder which generates very high forces used to press the material out through small holes in the extruder head. The extrudate is of uniform diameter and is then transferred onto a rotating plate for spheronization. The forces generated by the rotating plate initially break up the extruded formulation strands into uniform lengths. Additional dwell time within the spheronizer creates particles which are quite round and very uniform in size. These pellets or spheres must then be dried to the target moisture content, usually within a fluid bed system.

Particles produced in this manner tend to be very dense, and have a capacity for high drug loading, approaching 90% or more in some cases. Preferably, particle size is uniform, and the size distribution is narrow, as compared to other granulation approaches. This quality assures consistent surface area within and between batches, which is desired when functional coatings are subsequently applied to create sustained release formulations, delayed release formulations and formulations designed to target a specific area within the body.

Uniform surface area is desired because the pharmaceutical coating process endpoint is determined not by coating thickness, but by the theoretical batch weight gain of the coating material. If the batch surface area is consistent, then the coating thickness will also be consistent for a given weight gain, and coating thickness is the primary variable in determining the functionality of the coating system, whether the goal is controlling the duration of sustained release formulations or imparting an acid resistant characteristic to "beads" necessary to protect certain compounds which would otherwise be severely degraded in the presence of the acidic environment of the stomach.

E. Spray Drying

Spray drying is a unique and specialized process which converts liquids into dry powders. The process involves the spraying of very finely atomized droplets of solution into a "bed" or stream of hot process air or other suitable gas. Not typically utilized for the conventional granulation of dosage form intermediates, spray drying has gained acceptance within the industry as a robust process which can improve drug solubility and bioavailability.

Spray drying can be used to create co-precipitates of a drug/carrier which can have improved dissolution and solubility characteristics. In addition, the process can also be useful as a processing aid. For example, it is much more difficult to maintain the uniformity of a drug in suspension, as compared to the same compound in solution. One may have a need to develop an aqueous coating or drug layering process utilizing a drug which is otherwise not soluble in water. By creating a co-precipitate of the drug and a suitable water soluble carrier, often a low molecular weight polymer, the co-precipitate will remain in solution throughout the manufacturing process, improving uniformity of the spray solution and the dosage form created by the coating process. Uniformity is particularly desired where lower doses of potent compounds are intended to be coated onto beads or tablet cores.

This same process may be used to enhance the solubility and bioavailability of poorly soluble drugs. By complexing certain excipients and the active ingredient within a solvent system which is then spray dried, it is possible to enhance the drugs absorption within the body. Selection of the solvent system, the complexing agent(s) and the ratios utilized within the formulation are all formulation variables which determine the effectiveness of solubility enhancement utilizing the spray drying technique. Process parameters which also have an effect on drug solubility are the temperatures of the spray solution and process gas, the spray rate and droplet size and the rate of re-crystallization. The spray dried granulations created by these techniques can then be incorporated into capsules or tablets by conventional manufacturing processes.

IV. METHODS OF MAKING THE EXTENDED RELEASE GASTRIC RETENTIVE DOSAGE FORMS DISCLOSED HEREIN

In one aspect, a method of making a gastric retentive extended-release dosage form as a single layer tablet comprising dry blending of the acamprosate with the binder is provided. The blended material is then granulated in the presence of water using, for example, a KitchenAid® blender. The granulated particles are then dried overnight, screened and blended with additional excipients as needed to form a mixture which is then compressed to form tablets.

Extended release polymer matrices comprising acamprosate are made using one or a combination of one or more of the following: POLYOX® 1105 (approximate molecular weight of 900,000 Daltons), POLYOX® N-60K (approximate molecular weight of 2,000,000 Daltons), POLYOX® WSR-301 (approximate molecular weight of 4,000,000 Daltons), or POLYOX® WSR-303 (approximate molecular weight of 7,000,000 Daltons).

After granulation of the active ingredient and subsequent blending the additional excipients, batches are characterized with respect to properties such as final Loss on Drying (LOD), bulk density, tap density, and particle size.

Loss on Drying (LOD) is determined after each granulation using the Moisture Analyzer. A 1 g samples are taken and loaded into the moisture analyzer. The sample is run for 5 minutes at a temperature of 105° C.

Bulk and tap densities can be determined as follows. A graduated cylinder is filled with a certain amount of material (82-88 g), and the volume recorded to determine the material bulk density. Tap density can be determined with a help of a Tap Density Tester by exposing the material to 100 taps per test and recording the new volume.

Particle size determination is performed immediately after granulation, after sieving through 20 mesh screen to remove agglomerates. Particle diameter is determined with a sieve-type particle diameter distribution gauge using sieves with openings of 44, 53, 75, 106, 150, and 250 mesh. Fractions are weighed on Mettler balance to estimate size distribution. This provides determination of the quantitative ratio by particle diameter of composition comprising extended release particles. Sieve analysis according to standard United States Pharmacopoeia methods (e.g., USP-23 NF 18), may be done such as by using a Meinzer II Sieve Shaker.

The granulated mixture can be blended with the polymer, filler and lubricant in a V-blender. The resultant mixture can be compressed into monolithic, single-layer tablets using, for example, a Piccola Press or a Manesty® BB4 press, with the appropriate tooling.

Tablets may then be characterized with respect to disintegration and dissolution release profiles as well as tablet hardness, friability and content uniformity.

The dissolution and disintegration profiles for the tablets may be determined using a USP Dissolution Apparatus I, II or III tester or a USP Disintegration tester, as is well known in the art. Tests may be performed, for example, at about pH 1.2 (modified simulated gastric fluid, or mSFG), about pH 4.5 (the approximate pH of the stomach after a meal), about pH 6.8 or at about pH 7.5, at 37° C. Suitable aliquots of the release rate solutions are tested to determine the amount of drug released from the dosage form or pharmaceutical composition. For example, the drug can be assayed or injected into a chromatographic system to quantify the amounts of drug released during the testing intervals.

A tablet must disintegrate before it dissolves. A disintegration tester measures the time it takes a tablet to break apart in solution. The tester suspends tablets in a solution bath for visual monitoring of the disintegration rate. Both the time to disintegration and the disintegration consistency of all tablets are measured. Samples, 1 ml at each time-point, may be taken, for example, without media replacement at 0.125, 0.25, 0.5, 1, 2, 3, 4, 5, 6, 7 and 8 hours. The resulting cumulative disintegration profiles are based upon a theoretical percent active added to the formulation is determined.

Tablet hardness changes rapidly after compression as the tablet cools. A tablet that is too hard may not break up and dissolve into solution before it passes through the body. In the case of the presently disclosed gastric retentive dosage forms, a tablet that is too hard may not be able to imbibe fluid rapidly enough to prevent passage through the pylorus in a stomach in a fed mode. A tablet that is too soft may break apart, not handle well, and can create other defects in manufacturing. A soft tablet may not package well or may not stay together in transit.

After tablets are formed by compression, it is desired that the tablets have a strength of at least 9-25 Kiloponds (Kp)/cm$^2$, preferably at least about 12-20 (Kp)/cm$^2$. A hardness tester is used to determine the load required to diametrically break the tablets (crushing strength) into two equal halves. The fracture force may be measured using a Venkel Tablet Hardness Tester, using standard USP protocols.

Friability is a well-known measure of a tablet's resistance to surface abrasion that measures weight loss in percentage after subjecting the tablets to a standardized agitation procedure. Friability properties are especially relevant during any transport of the dosage form as any fracturing of the final dosage form will result in a subject receiving less than the prescribed medication. Friability can be determined using a Roche Friability Drum according to standard USP guidelines which specifies the number of samples, the total number of drum revolutions and the drum rpm to be used. Friability values of from 0.8 to 1.0% are regarded as constituting the upper limit of acceptability.

The prepared tablets may be tested for content uniformity to determine if they meet the pharmaceutical requirement of <6% relative standard deviation (RSD). Each tablet is placed in a solution of 1.0 N HCl and stirred at room temperature until all fragments have visibly dissolved. The solution containing the dissolved tablet is analyzed by HPLC.

In one aspect, a method of making a bilayer tablet comprising a gastric retentive extended-release layer and an immediate release layer is provided.

IV. STABILITY OF ACAMPROSATE EXTENDED RELEASE FORMULATIONS

Stability testing is the primary tool used to assess expiration dating and storage conditions for pharmaceutical products. Many protocols have been used for stability testing, but most in the industry are now standardizing on the recommendations of the International Conference on Harmonization (ICH). These guidelines were developed as a cooperative effort between regulatory agencies and industry officials from Europe, Japan, and the United States.

Stability testing includes long-term studies, where the product is stored at room temperature and humidity conditions, as well as accelerated studies where the product is stored under conditions of high heat and humidity. Proper design, implementation, monitoring and evaluation of the studies are crucial for obtaining useful and accurate stability data. Stability studies are linked to the establishment and assurance of safety, quality and efficacy of the drug product from early phase development through the lifecycle of the drug product. Stability data for the drug substance are used to determine optimal storage and packaging conditions for bulk lots of the material. The stability studies for the drug product are designed to determine the expiration date (or shelf life). In order to assess stability, the appropriate physical, chemical, biological and microbiological testing must be performed. Usually this testing is a subset of the release testing.

Studies are designed to degrade the solid drug substance and appropriate solutions, allowing the determination of the degradation profile. The drug substance is usually challenged under a variety of accelerated environmental conditions to evaluate its intrinsic stability and degradation profile.

HPLC is the predominant tool used to analyze the drug substance and the impurities, particularly for small molecules. Frequently, the same HPLC method may be used for drug substance and drug product, although different sample preparation methods would normally be required. Often the assay and impurity testing can be performed using a single HPLC method. However, the assay and purity determinations may also be separate methods. At least in the U.S., full validation of the analytical method is not required until the end of Phase 2 clinical trials, but the establishment of specificity, linearity and limit of quantification (for impurities) is considered at the earliest stages, since verification of stability hinges on a suitable method for separating impurities from the active ingredient and at least quantifying the impurities relative to the drug substance.

Stress studies at elevated temperature (e.g., 50° C., 60° C. and 70° C.) for several weeks may be performed to assess thermal stability. Provided the degradation mechanism is the same at the different temperatures used, kinetic or statistical models can be used to determine the rate of degradation at other temperatures (e.g., 25° C.). The solid stability should also be performed in the presence and absence of water vapor to assess the dependence of stability on humidity.

Degradation studies should also be performed in solution. The solvent used for the solution testing will depend on the solubility of the drug substance and should include water, if the drug substance is water-soluble. Other solutions or solvent systems may be evaluated depending on the anticipated formulation or the synthetic process. A series of buffered solutions in the pH range 2-9 are useful in assessing the impact of solution pH on the degradation. Photostability should also be evaluated. A xenon light source can be used as a stress condition. Alternatively, one can use an accelerated version of either Options 1 or 2 as described in the ICH guideline for determination of photostability. Oxidation of the drug substance under accelerated conditions (e.g., hydrogen peroxide), may also be performed to establish oxidation products that could be formed and sensitivity to oxidative attack.

Early drug product stability studies are designed to help establish a suitable formulation for delivery of the drug substance. Compatibility studies of the drug substance with excipients should be performed to eliminate excipients that are not compatible with the drug substance.

V. METHODS OF TREATMENT

In another aspect, the dosage form comprising acamprosate is administered to a subject suffering from alcohol dependence, tinnitus, sleep apnea, Parkinson's disease, levodopa-induced dyskinesias in Parkinson's disease, Alzheimer's disease, Huntington's disease, Amyotrophic lateral sclerosis, Cortical spreading depression, migraine, schizophrenia. Anxiety, tardive dyskinesia, spasticity, multiple sclerosis, various types of pain, or binge eating.

Generally, the frequency of administration of a particular dosage form is determined to provide the most effective results in an efficient manner without overdosing and varies according to the following criteria: (1) the characteristics of the particular drug(s), including both its pharmacological characteristics and its physical characteristics, such as solubility; (2) the characteristics of the swellable matrix, such as its permeability; and (3) the relative amounts of the drug and polymer. In most cases, the dosage form is prepared such that effective results are achieved with administration once every six hours, once every eight hours, once every twelve hours, or once every twenty-four hours. As previously discussed, due to the physical constraints placed on a tablet or capsule that is to be swallowed by a patient, most dosage forms can only support a limited amount of drug within a single dosage unit.

In one embodiment, the dosage form allows a dosing frequency of once a day (q.d.) or twice a day (b.i.d.) to provide a sustained concentration of acamprosate in the subject's blood as compared to current immediate release products which require more frequent administration for effective sustained therapy.

Within the context of the present disclosure, the gastric retentive dosage forms have the added advantage of improving patient compliance with administration protocols because the drugs may be administered in a once-daily or twice-daily dosing regimen, while still minimizing side effects associated with high doses and/or low concentrations of the active agent (e.g., acamprosate) which result from commercially available forms of acamprosate.

For all modes of administration, the gastric retentive dosage forms described herein are preferably administered in the fed mode, i.e., with or just after consumption of a small meal (see U.S. Publication No. 2003/0104062, herein incorporated by reference).

In some aspects, the postprandial or fed mode can also be induced pharmacologically, by the administration of pharmacological agents that have an effect that is the same or similar to that of a meal. These fed-mode inducing agents may be administered separately or they may be included in the dosage form as an ingredient dispersed in the shell, in both the shell and the core, or in an outer immediate release coating. Examples of pharmacological fed-mode inducing agents are disclosed in U.S. Pat. No. 7,405,238, entitled "Pharmacological Inducement of the Fed Mode for Enhanced Drug Administration to the Stomach," the contents of which are incorporated herein by reference.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the present disclosure or its claims.

EXAMPLES

The following examples are intended to illustrate the dosage forms, methods of manufacture, and methods of treatment, and are not intended to limit the disclosure.

Example 1

Preparation of Gastric Retentive Dosage Forms for Extended Release of Acamprosate Two formulations of extended release acamprosate tablets, each containing 666 mg acamprosate calcium and 17 wt % POLYOX 303 (average molecular weight of 7,000,000 Da) were initially produced. Formula I: 66.6 wt % acamprosate calcium, 4 wt % polyvinylpovidone (PVP), 17 wt % POLYOX 303, 11.9 wt % Ceolus KG-1000 and 0.5 wt % magnesium stearate. Formula II: 66.6 wt % acamprosate calcium, 4 wt % polyvinylpyrrolidone (PVP), 17 wt % POLYOX 303, 11.9 wt % Eudragit RS PO, and 0.5 wt % magnesium stearate. These two formulas differed in the inclusion of the Eudragit RS PO vs. Ceolus KG-1000 polymers. Ceolus KG-1000 is a microcrystalline cellulose made with a very high aspect ratio. It may be used in small quantities to increase the compactability and hardness, and reduce friability of formulations, compared to other grades of microcrystalline cellulose. Eudragit RS PO, and the related RL PO grade, are insoluble polymers which include a quaternary amine. Reasons for using Eudragit RS PO include: to provide some swelling, to function as an insoluble excipient to slow the rate of hydration and further retard release of the drug, and to provide a cationic charge (via the quaternary amines on the polymer) to interact with the anionic acamprosate molecule to further retard release. Tablets were manufactured using a dry blend process in which excipients were blended in 2 oz glass jars. After each excipient was added, the blends were stirred by hand. The entire blen was then mixed for 2 minutes in the jar on a Turbula Mixer. Tablets having a total mass of 1000 mg were hand made on a Carver Auto C Press (Fred Carver, Inc., Indiana) and compressed into tablets using a 0.4330"×0.7450" Modified Oval die (Natoli Engineering, St. Charles, Mo.). The parameters for the operation of the Carver Auto C Press are as follows: 2000 lbs compression force, 0 second dwell time (the setting on the Carver Press), and 100% pump speed.

Dissolution profiles were determined in a USP Dissolution Apparatus I tester in 900 ml modified simulated gastric fluid, pH 1.2, 40 mesh, 100 rpm, at 37° C. Samples, 1 ml at each time-point, were taken without media replacement at 1, 2, 4, 6, 8 and 12 hours. The cumulative dissolution results, based upon a theoretical percent active added to the formulation, are determined.

Release profiles for the Formula I and II tablets are presented below in Tables 1 and 2 and are graphically represented in FIGS. 1 and 2.

TABLE 1

| Lot# Formula I, 666 g Acamprosate Calcium | | | | | | |
|---|---|---|---|---|---|---|
| | Acamprosate Calcium Cumulative Released (%) | | | | | |
| | Hours | | | | | |
| | 1 | 2 | 4 | 6 | 8 | 12 |
| #1 | 27.4 | 44.2 | 66.4 | 80.1 | 89.3 | 96.9 |
| #2 | 25.3 | 41.5 | 63.8 | 78.2 | 87.4 | 95.8 |
| Average | 26.4 | 42.8 | 65.1 | 79.2 | 88.4 | 96.3 |
| StdDev | 1.44 | 1.95 | 1.86 | 1.33 | 1.38 | 0.77 |
| % CV | 5.46 | 4.55 | 2.85 | 1.67 | 1.56 | 0.80 |

TABLE 2

Lot# Formula II, 666 g Acamprosate Calcium

Acamprosate Calcium Cumulative Released (%)
Hours

|  | 1 | 2 | 4 | 6 | 8 | 12 |
|---|---|---|---|---|---|---|
| #1 | 28.7 | 45.0 | 66.8 | 80.3 | 88.2 | 96.4 |
| #2 | 27.4 | 44.4 | 67.4 | 81.6 | 90.3 | 97.6 |
| Average | 28.1 | 44.7 | 67.1 | 81.0 | 89.3 | 97.0 |
| StdDev | 0.89 | 0.46 | 0.43 | 0.86 | 1.54 | 0.83 |
| % CV | 3.18 | 1.02 | 0.64 | 1.06 | 1.72 | 0.86 |

The dissolution results show that both Formula I and Formula II tablets were successful in providing a release of the acamprosate calcium over a period of at least 12 hours, with a release of about 90% between about 8 and 12 hours.

Additional tablets were formulated to study the effects of POLYOX 1105 (average molecular weight of 900,000) and Pearlitol 100 SD, a fine particle of the soluble excipient mannitol. Pearlitol increases the rate of hydration to increase the rate of release and swelling by drawing dissolution media into the hydrating tablet faster than would an insoluble excipient or POLYOX. Pearlitol also dissolves, leaving behind pores through which drug can freely diffuse.

Tablets having Formula III: 66.6 wt % acamprosate calcium, 4 wt % PVP, 23.9 wt % POLYOX 303, 5 wt % Ceolus KG-1000 and 0.5 wt % Mg stearate, Formula IV: 66.6 wt % acamprosate calcium, 4 wt % PVP, 17 wt % POLYOX 303, 6.9 wt % POLYOX 1105, 5 wt % Ceolus KG-1000 and 0.5 wt % Mg stearate, and Formula V: 66.6 wt % acamprosate calcium, 4 wt % PVP, 17 wt % POLYOX 303, 11.9 wt % Pearlitol, and 0.5 wt % Mg stearate. Dissolution studies were carried out as described for Formulas I and II and the data are presented below in Tables 3, 4, and 5.

TABLE 3

Formula III, 666 g Acamprosate Calcium

Acamprosate Cumulative Released (%)
Hours

|  | 1 | 2 | 4 | 6 | 8 | 12 |
|---|---|---|---|---|---|---|
| #1 | 24.0 | 39.3 | 61.5 | 75.8 | 86.0 | 95.4 |
| #2 | 24.4 | 39.8 | 61.6 | 76.1 | 85.8 | 95.3 |
| Average | 24.2 | 39.6 | 61.5 | 76.0 | 85.9 | 95.3 |
| Std Dev | 0.28 | 0.34 | 0.06 | 0.24 | 0.14 | 0.08 |
| % CV | 1.15 | 0.85 | 0.10 | 0.32 | 0.17 | 0.08 |

TABLE 4

Formula IV-TDRF, 666 g Acamprosate Calcium

Acamprosate Cumulative Released (%)
Hours

|  | 1 | 2 | 4 | 6 | 8 | 12 |
|---|---|---|---|---|---|---|
| #1 | 27.2 | 42.6 | 64.8 | 78.7 | 88.1 | 96.2 |
| #2 | 27.7 | 43.2 | 64.9 | 79.4 | 88.6 | 96.7 |
| Average | 27.4 | 42.9 | 64.9 | 79.0 | 88.3 | 96.5 |
| Std Dev | 0.34 | 0.44 | 0.09 | 0.44 | 0.35 | 0.34 |
| % CV | 1.23 | 1.02 | 0.14 | 0.56 | 0.40 | 0.35 |

TABLE 5

Formula V-TDRF, 666 g Acamprosate Calcium

Acamprosate Cumulative Released (%)
Hours

|  | 1 | 2 | 4 | 6 | 8 | 12 |
|---|---|---|---|---|---|---|
| #1 | 28.9 | 45.5 | 68.0 | 81.5 | 90.5 | 97.5 |
| #2 | 28.1 | 45.0 | 67.5 | 81.7 | 90.3 | 97.2 |
| Average | 28.5 | 45.2 | 67.8 | 81.6 | 90.4 | 97.3 |
| Std Dev | 0.58 | 0.35 | 0.37 | 0.16 | 0.17 | 0.19 |
| % CV | 2.03 | 0.78 | 0.55 | 0.19 | 0.19 | 0.20 |

Figure 2:
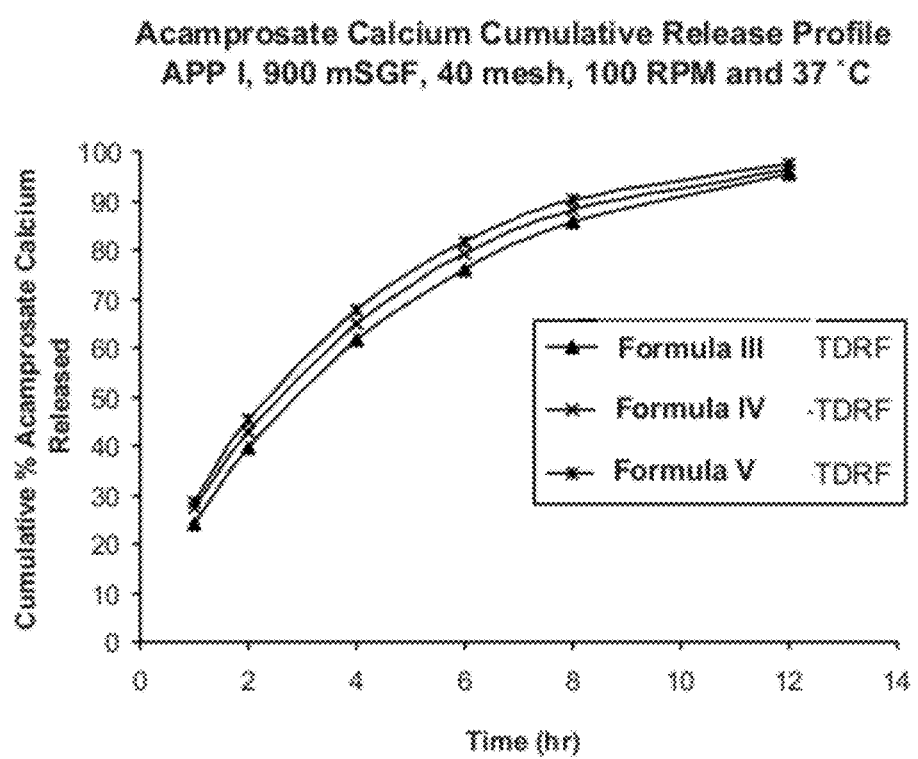
FIG. 2 is a graph showing release of acamproste calcium from extended release dosage forms.

The data are shown schematically in FIG. 2. Again, the formulations were successful in providing a release of the acamprosate over a period of at least 12 hours with about 90% release occurring within 8-12 hours after submersion in fluid.

Example 2

Swelling and Erosion Profiles of Gastric Retentive Extended-Release Acamprosate Tablets The swelling and erosion profiles of acamprosate dosage forms are assessed by monitoring weight change with time. Tablets are tested using an Apparatus III (250 ml) USP Disintegration Tester in pH 4.5 acetate buffer or in pH 7.5 phosphate buffer, at 37° C. Tablets are tested at time points between 0.25 and 8 hours. Each tablet is weighed, dried overnight at 50° C., then reweighed.

Example 3

Bioavailability Studies in Dogs

A study was performed to evaluate the pharmacokinetics of acamprosate delivered from an IR formulation as compared to acamprosate delivered via simulated extended release (SER). Because acamprosate is absorbed only in the upper small intestine and its absorption is known to be less than dose proportional, absorption is likely limited by permeability through the intestinal lining rather than dissolution from the oral dosage form. Accordingly, bioavailability may be improved by a gastric retentive extended-release formulation of acamprosate. Slow, continuous bathing of the upper small intestinal wall with a solution of acamprosate may provide increased bioavailability as compared to bioavailability achieved upon the single bolus provided by an immediate release oral dosage form.

This study was conducted in 5 healthy beagle dogs weighing between 12-16 kg to determine relative bioavailability of acamprosate when administered orally via the SER formulation as compared to the IR formulation (as a soft gel capsule). Following an overnight fast of at least 12 hours, the dogs were fed 100 g canned dog food (Pedigree@ Traditional ground Dinner with Chunky Chicken). The SER dosing was designed to simulate a linear release with the square root of time over a period of about 8 hours. The dosing schedule of the SER acamprosate arm is presented below as Table 3.

TABLE 3

| Time (h) | Amount (mg) |
|---|---|
| 0 | 81.2 |
| 0.5 | 33.6 |
| 1.0 | 25.8 |

TABLE 3-continued

| Time (h) | Amount (mg) |
|---|---|
| 1.5 | 21.8 |
| 2.0 | 19.2 |
| 2.5 | 17.3 |
| 3.0 | 15.9 |
| 3.5 | 14.8 |
| 4.0 | 13.9 |
| 4.5 | 13.2 |
| 5.0 | 12.5 |
| 5.5 | 12.0 |
| 6.0 | 11.5 |
| 6.5 | 11.1 |
| 7.0 | 10.7 |
| 7.5 | 10.3 |
| Total Dose | 324.8 |

Blood samples were drawn via venipuncture from the cephalic vein at 0.5 h, 1.0 h, 2.0 h, 3.0 h, 4.0 h, 5.0 h, 6.0 h, 8.0 h, 10.0 h, 12.0 h and 24 h post-dose. Samples were analyzed by LC-MS to determine acamprosate concentration. $AUC_{0-t}$ was calculated using non-compartmental analysis (WinNonlin). $C_{max}$ and $t_{max}$ were obtained from inspection of individual plasma concentration-time data. Relative bioavailability of the SER to the comparator (IR formulation) was calculated by dividing the AUC of the SER by the comparator's AUC. A paired t test on the ln transformed AUC and $C_{max}$ was used to determine if there was a significant difference. A p value of <0.05 was considered to be statistically significant. A Wilcoxon signed-ranks test was used to determine if there was a significant different between tmax values.

Figure 3:
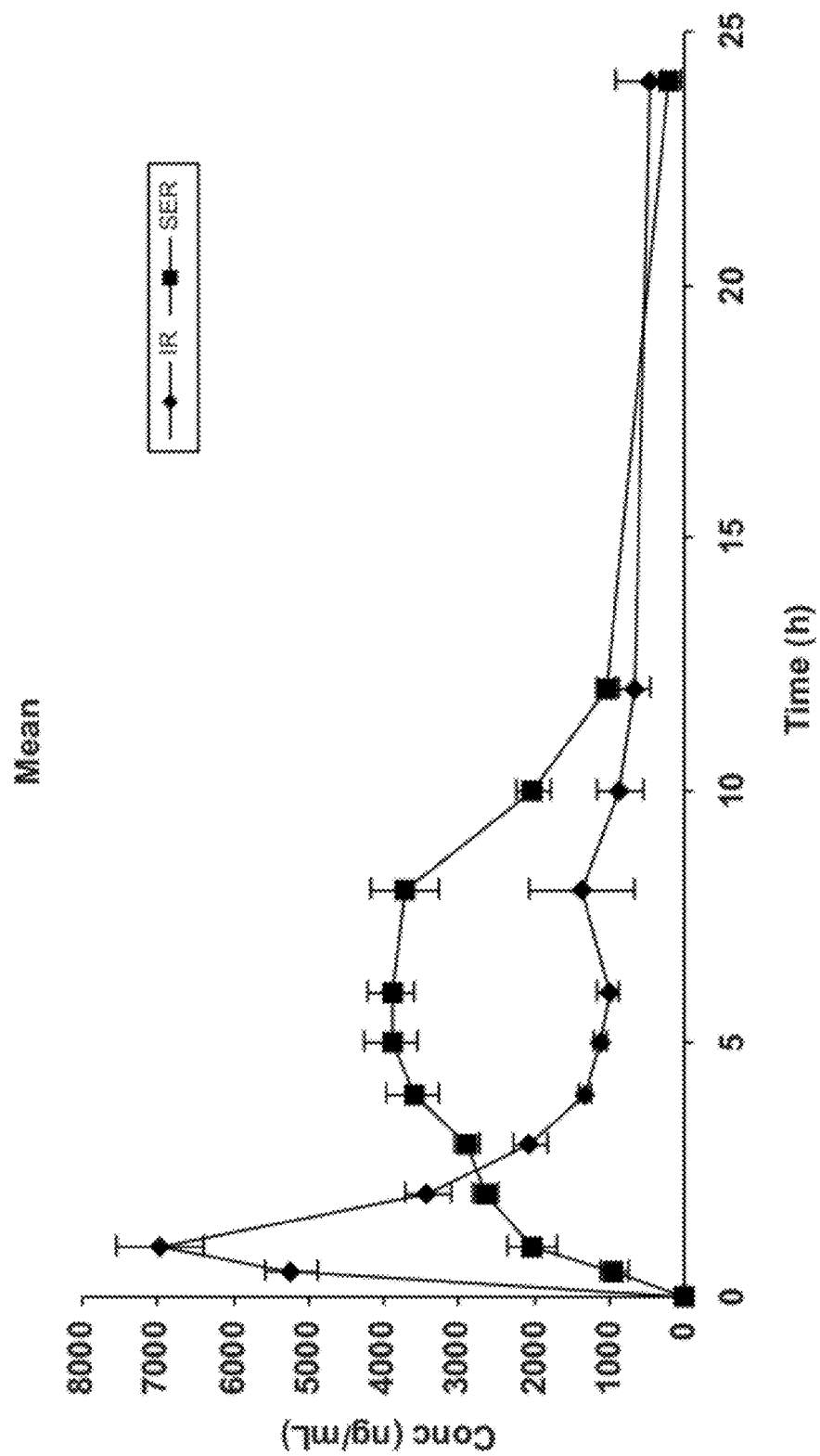
FIG. 3 is a graph showing plasma concentrations over time after administration of acamprosate calcium to dogs.

Results of the study are presented in Table 4 and presented schematically in FIG. 3. As expected, a rapid rise in acamprosate plasma concentration was observed with the IR formulation, in which an average Cmax of 6976±1180 was obtained as compared to the average Cmax of 4428±683 achieved with the SER dosing. The mean bioavailability of the SER formulation was about 154% of the IR formulation as calculated from the AUC values.

TABLE 4

| Dog # | $AUC_{0-t}$ IR (ng · h/mL) | $AUC_{0-t}$ SER (ng · h/mL) | R-BA (%) | $C_{max}$ IR (ng/mL) | $C_{max}$ SER (ng/mL) |
|---|---|---|---|---|---|
| 1 | 31939 | 35185 | 110 | 7380 | 4620 |
| 2 | 31829 | 44221 | 1339 | 7150 | 5140 |
| 3 | 35345 | 39182 | 111 | 7550 | 4510 |
| 4 | 15929 | 32243 | 202 | 4920 | 3290 |
| 5 | 21520 | 44786 | 208 | 7880 | 4580 |
| Mean ± SD | 27312 ± 8208 | 39123 ± 5498 | 154 ± 48 | 6976 ± 1180 | 4428 ± 683 |
| p value | | 0.0359 | | | 0.0013 |

Example 4

Erosion Studies with Gastric Retentive Extended-Release Acamprosate Tablets in Beagle Dogs This study is conducted in 4 or 5 healthy beagle dogs weighing between 12-16 kg to determine the erosion time of different formulations of gastric retentive extended-release acamprosate tablets. Following an overnight fast of at least 14 hours, the dogs are fed 100 g of canned dog food (Pedigree@ Traditional ground Dinner with Chunky Chicken). Within 15 minutes of the dog consuming the meal they are administered one of the acamprosate tablet formulations. Each dog receives each formulation. There are at least 2 days between administrations of a first and second formulation, and then a period of about 6 month elapsed before a third and fourth formulation is administered. Erosion of the gastric retentive extended-release tablets is assessed using fluoroscopy. Each tablet contains two radio-opaque strings in the shape of an "X". Separation of the strings is considered to signify complete erosion of the tablets. Images are obtained every 30 minutes until the strings separate. The recorded erosion time is the midpoint between the last time the tablet was intact and when the strings are separated. From the dog erosion study a prediction of delivery (erosion) time is calculated based on a correlation developed between dog and human from previous erosional tablet studies.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A gastric retentive dosage form comprising, a dose of acamprosate or a pharmaceutically acceptable salt thereof dispersed in a polymeric matrix wherein the polymeric matrix comprises one or more polymers that upon imbibition of fluid swells to a size sufficient to promote gastric retention, wherein upon administration to the subject, the gastric retentive dosage form provides a mean AUC of plasma acamprosate which is at least 50% greater than the mean AUC of plasma acamprosate provided by an immediate release (IR) dosage form which contains a dose of acamprosate or pharmaceutically acceptable salt thereof equal to or more than the dose of acamprosate in the gastric retentive dosage form.

2. The dosage form of claim 1, wherein the gastric retentive dosage form provides a mean $C_{max}$ of plasma acamprosate which is about 60% to 70% of the mean $C_{max}$ of plasma acamprosate provided by the IR dosage form.

3. The dosage form of claim 1, wherein the gastric retentive dosage form provides a $T_{max}$ which is about 3 hours to 8 hours greater than the $T_{max}$ provided by the IR dosage form.

4. The dosage form of claim 1, wherein administration to a subject in a fed mode results in a decrease in mean AUC of plasma acamprosate which is less than about 10% of the AUC when the dosage form is administered to the subject in a fasted state.

5. The dosage form of claim 1, wherein the side effects of the gastric retentive dosage form having no enteric coating are equal to or less than the immediate release dosage form having an enteric coating.

6. The dosage form of claim 1, wherein the dose of acamprosate is about 200 mg to about 1000 mg.

7. The dosage form of claim 1, wherein not less than about 60% of the dose of acamprosate is released from the gastric retentive dosage form after about 6 hours after exposure to fluid.

8. The dosage form of claim 1, wherein the at least one or more polymers is a polyethylene glycol having a molecular weight of about 900,000 daltons to about 10,000,000 daltons.

9. A method for treating a subject suffering from alcohol dependence comprising administering to the subject a total daily dose of about 300 mg to 2500 mg acamprosate or a pharmaceutically acceptable salt thereof dispersed in a polymeric matrix wherein the polymeric matrix comprises one or more polymers that upon imbibition of fluid swells to a size sufficient to promote gastric retention, wherein upon administration to the subject, the gastric retentive dosage form provides a mean AUC of plasma acamprosate which is at least 50% greater than the mean AUC of plasma acamprosate provided by an immediate release (IR) dosage form which contains a dose of acamprosate or pharmaceutically acceptable salt thereof equal to or more than the dose of acamprosate in the gastric retentive dosage form.

10. The method of claim 9, wherein said dose is administered twice in a 24-hour period.

11. The method of claim 9, wherein said dose is administered once in a 24-hour period.

* * * * *